(12) United States Patent
Kaur et al.

(10) Patent No.: US 8,541,178 B2
(45) Date of Patent: Sep. 24, 2013

(54) ANALYSIS OF ANTIBODY DRUG CONJUGATES BY BEAD-BASED AFFINITY CAPTURE AND MASS SPECTROMETRY

(75) Inventors: Surinder Kaur, Lafayette, CA (US); Ola Saad, Walnut Creek, CA (US); Keyang Xu, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 637 days.

(21) Appl. No.: 12/464,250

(22) Filed: May 12, 2009

(65) Prior Publication Data

US 2009/0286258 A1    Nov. 19, 2009

Related U.S. Application Data

(60) Provisional application No. 61/052,727, filed on May 13, 2008.

(51) Int. Cl.
*G01N 33/53* (2006.01)
*A61K 39/395* (2006.01)

(52) U.S. Cl.
USPC ....... 435/7.1; 424/9.2; 424/178.1; 424/181.1; 530/413; 530/391.7; 530/391.9

(58) Field of Classification Search
None
See application file for complete search history.

(56) References Cited

U.S. PATENT DOCUMENTS

| | | | |
|---|---|---|---|
| 6,020,208 A | 2/2000 | Hutchens et al. | |
| 6,172,197 B1 * | 1/2001 | McCafferty et al. | 530/387.3 |
| 7,329,353 B2 | 2/2008 | Dillon et al. | |
| 2002/0197694 A1 | 12/2002 | Shao | |
| 2003/0027216 A1 | 2/2003 | Kiernan et al. | |
| 2005/0232929 A1 | 10/2005 | Kadkhodayan et al. | |

FOREIGN PATENT DOCUMENTS

| WO | WO 03/046571 | 5/2003 |
|---|---|---|
| WO | WO 03/046572 | 9/2009 |

OTHER PUBLICATIONS

Whiteaker et al. "Antibody-based enrichment of peptides on magnetic beads for mass-spectrometry-based quantification of serum biomarkers," Analytical Biochemistry, Mar. 1, 2007, vol. 362, issue 1, pp. 44-54; Available online Dec. 20, 2006.*
Keyang Xu; Ola M. Saad; Jakub Baudys; Lara Williams; Surinder Kaur (Xu et al.) "Bioanalytical Strategies for Antibody Drug Conjugate (ADC) Biopharmaceutical Development: Characterization of Trastuzumab-MCC-DM1 in Plasma by Affinity Mass Spectrometry," Poster presented on Jun. 25, 2007 at 2007 AAPS National Biotechnology Conference.*
"DynabeadsR M-280 Streptavidin" (protocol instructions for Catalog No. 112.05D, Rev No. 013, Oct. 2007, Invitrogen Dynal AS, Oslo, Norway).
"KingFisherR DynabeadsR TALONT Customer Solution" (Product Bulletin, Nov. 2003, Thermo Electron Co.).
"MagnaBindT Carboxyl Derivatized Beads" (Product Bulletin No. 21353, Sep. 2004).
(International Search Report for International Patent Application No. PCT/US2005/011675) mailed Sep. 21, 2005.
(International Search Report for International Patent Application No. PCT/US2009/043560) mailed Sep. 10, 2009.
Abdel-Hamid et al., "Liquid chromatographic-mass spectrometric determination of celecoxib in plasma using single-ion monitoring and its use in clinical pharmacokinetics" *J. of Chrom.* B 753:401-408 (2001).
Alley, S.C. et al., "Controlling the location of drug attachment in antibody-drug conjugates, Abstract No. 627, American Association for Cancer Research, 2004 Annual Meeting, Mar. 27-31, 2004 Proceedings of the AACR" 45:52 (2004).
Beaudry, F. et al., "In Vivo pharmacokinetic screening in cassette dosing experiments: the use of on-line Prospekt$^R$ liquid chromatography/atmospheric pressure chemical ionization tandem mass spectrometry technology in drug discovery" Rapid Commun. Mass Spectrom. 12:1216-1222 (1998).
Bier, Mark E., "Analysis of proteins by mass spectrometry" *Modern Protein Chemistry*, Howard and Brown, CRC Press, Chapter 4, pp. 71-88 (2002).
Bourdage, J.S. et al., "Effect of double antigen bridging immunoassay format on antigen coating concentration dependence and implications for designing immunogenicity assays for monoclonal antibodies" J. Pharm. Biomed. Analysis 39:685-690 (2005).
DiJoseph et al., "Antibody-targeted chemotherapy with CMC-544: a CD22-targeted immunoconjugate of calicheamicin for the treatment of B-lymphoid malignancies" *Blood* 103:1807-1814 (2004).
Doronina et al., "Development of potent monoclonal antibody auristatin conjugates for cancer therapy" *Nature Biotechnology* 21:778-784 (2003).
Francisco et al., "cAC10-vcMMAE, an anti-CD30 monomethyl auristatin E conjugate with potent and selective antitumor activity" *Blood* 102:1458-1465 (2003).
Hamblett, K. J. et al., "Effect of drug loading on the pharmacology, pharmacokinetics and toxicity of an anti-CD30 antibody-drug conjugate, Abstract No. 624, American Association for Cancer Research; 2004 Annual Meeting, Mar. 27-31, 2004, Proceedings of the AACR" 45:52 (2004).

(Continued)

*Primary Examiner* — Shafiqul Haq
*Assistant Examiner* — Galina Yakovleva
(74) *Attorney, Agent, or Firm* — Alex Andrus; Genentech, Inc.

(57) ABSTRACT

Methods to detect, characterize, and quantitate biological samples after administration of antibody conjugates, antibody-drug conjugates of Formula I, antibodies, and fragments and metabolites thereof, by immunoaffinity bead separation, chromatography, and mass spectrometry are disclosed;

Ab-(L-D)$_p$    I wherein
Ab is an antibody;
D is a drug moiety;
L is a linker covalently attached to Ab, and covalently attached to D; and
p is 1, 2, 3, 4, 5, 6, 7, or 8.

30 Claims, 12 Drawing Sheets

(56) References Cited

OTHER PUBLICATIONS

Hamblett, K.J. et al., "Effects of drug loading on the antitumor activity of a monoclonal antibody drug conjugate" *Clin. Cancer Res.* 10:7063-7070 (2004).

Kadkhodayan et al., "A novel approach to characterization of Trastuzumab-DM1 conjugates using LC-MS for confirmation of statistically calculated distributions, 51st Conference on Mass Spectrometry and Allied Topics, American Society for Mass Spectrometry, Montreal, Quebec, Jun. 8-12, 2003" (2003).

Kadkhodayan, M. and Mann, E., "New strategies in characterization and quantitation of antibody-targeted drug conjugates in plasma using LC/LC/MS, 51st Conference on Mass Spectrometry and Allied Topics, American Society for Mass Spectrometry, Montreal, Quebec, Jun. 8-12, 2003" (2003).

Kadkhodayan, M. and Mann, E., "Rapid antibody characterization and Quantitation using automated chip-based nanoelectrospray/MS, 52nd Conference on Mass Spectrometry and Allied Topics, American Society for Mass Spectrometry, Nashville, TN, May 23-27, 2004" (2004).

Kirchner et al., "Clinical pharmacokinetics of everolimus" *Clin. Pharmacokinetics* 43(2):83-95 (2004).

Kruppa et al., "Multiple ion isolation applications in FT-ICR MS: exact-mass MSn internal calibration and purification/interrogation of protein-drug complexes" *Anal Chem.* 74(15):3877-3886 (Aug. 1, 2002).

Mann and Kadkhodayan, "Antibody isolation and Quantitation using LC/MS and a novel 96-well immunoaffinity membrane" *52nd Conference on Mass Spectrometry and Allied Topics, American Society for Mass Spectrometry* (Nashville, TN, May 23-27, 2004).

Mao at al., "EphB2 as a Therapeutic Antibody Drug Target for the Treatment of Colorectal Cancer" *Cancer Research* 64:781-788 (2004).

Marques at al., "Enantioselective assay of nisoldipine in human plasma by chiral high-performance liquid chromatography combined with gas chromatographic-mass spectrometry: applications to pharmacokinetics" *J. Chrom.* 762:87-95 (2001).

Martin at al., "Antibody-directed enzyme prodrug therapy: pharmacokinetics and plasma levels of prodrug and drug in a phase I clinical trial" *Cancer Chemother. Pharmacol.* 40:189-201 (1997).

Murray, S. et al., "Identification of human serum interferants in the recombinant P-selectin glycoprotein ligand-1 clinical ELISA using MALDI MS and RP-HPLC" *J. Imm. Methods* 255:41-56 (2001).

Royer et al., "Paclitaxel metabolites in human plasma and urine: identification of 6α-hydroxytaxol, 7-epitaxol and taxol hydrolysis products using liquid chromatography/atmospheric-pressure chemical ionization mass spectrometry" *Rapid Comm. in Mass Spec.* 9:495-502 (1995).

Sanderson, R. J. et al., "In Vivo drug-linker stability of an anti-CD30 dipeptide-linked auristatin immunoconjugate" *Clin. Cancer Res.* 11:843-852 (2005).

Schlosser, G. et al., "Combination of solid-phase affinity capture on magnetic beads and mass spectrometry to study non-covalent interactions: example of minor groove binding drugs" *Rapid Commun. Mass Spectrom.* 19:3307-3314 (2005).

Senter et al., "Immunoconjugates comprised of drugs with impaired cellular permeability: a new approach to targeted therapy, Abstract No. 623, presented on Mar. 28, 2004, Proceedings of the American Association for Cancer Research" 45:36 (2004).

Siegel et al., "Calicheamicin derivatives conjugated to monoclonal antibodies: determination of loading values and distributions by infrared and UV matrix-assisted laser desorption/ionization mass spectrometry and electrospray ionization mass spectrometry" *Anal Chem.* 69(14):2716-2726 (Jul. 15, 1997).

Siegel et al., "Determination of loading values and distributions for drugs conjugated to proteins and antibodies by MALDI-MS and ESI-MS" *Methods Mol Biol.* 61:211-226 (1996).

Simpson, H. et al., "High throughput liquid chromatography/mass spectrometry bioanalysis using 96-well disk solid phase extraction plate for the sample preparation" (1998) *Rapid Commun. Mass Spectrom.* 12:75-82.

Souppart at al., "Development and validation of a high-performance liquid chromatography-mass spectrometry assay for the determination of artemether and its metabolite dihydroartemisinin in human plasma" *J. Of Chrom. B* 774:195-203 (2002).

Stephan, J-P. et al., "Anti-CD22-MCC-DM1 and MC-MMAF conjugates: impact of assay format on pharmacokinetic parameters determination" *Bioconjugate* 19:1673-1683 (2008).

Wong et al., "Liquid chromatography-mass spectrometry assay of a thiadiazole derivative in mice: application to pharmacokinetic studies" *J. of Chrom.* 765:55-62 (2001).

Xie et al, "Pharmacokinetics and biodistribution of the antitumor immunoconjugate, cantuzumab mertansine (huC242-DM1), and its two components in mice" *J Pharmacol Exp Ther.* 308(3):1073-1082 (Mar. 2004).

Yao et al., "Quantitation of itraconazole in rat heparinized plasma by liquid chromatography-mass spectrometry" *J. Chrom. B* 752:9-16 (2001).

Yao et al., "Sensitive liquid chromatographic-mass spectrometric assay for the simultaneous quantitation of nefazodone and its metabolites hydroxynefazodone m-chlorophenylpiperazine and triazole-dione in human plasma using single-ion monitoring" *J. of Chrom. B* 718:77-85 (1998).

Shen et al., "Conjugation site modulates the in vivo stability and therapeutic activity of antibody-drug conjugates" Nature Biotechnology 30(2):184-190 (Feb. 2012).

Xu et al., "Characterization of intact antibody-drug conjugates from plasma/serum in vivo by affinity capture capillary liquid chromatography-mass spectrometry" Analytical Biochemistry 412:56-66 (2011).

\* cited by examiner

Thio Hu Anti Her2 4D5 LC V205C
-MC-vc-PAB-MMAE (LC)

Thio Hu Anti Her2 4D5 HC A118C
-MC-vc-PAB-MMAE (HC)

Thio Hu Anti Her2 4D5 Fc S400C
-MC-vc-PAB-MMAE (FC)

Thio Hu Anti Her2 4D5 Fc S400C

Total ELISA

F(ab')2 goat anti-human Fc-HRP

Naked & ADC immobilized ECD

Conjugate ELISA

Streptavidin-HRP

Biotinylated ECD

ADC immobilized Anti-Drug MAb

US 8,541,178 B2

ANALYSIS OF ANTIBODY DRUG CONJUGATES BY BEAD-BASED AFFINITY CAPTURE AND MASS SPECTROMETRY

CROSS REFERENCE TO RELATED APPLICATIONS

This non-provisional application filed under 37 CFR §1.53 (b), claims the benefit under 35 USC §119(e) of U.S. Provisional Application Ser. No. 61/052,727 filed on 13 May 2008, which is incorporated by reference in entirety.

FIELD OF THE INVENTION

The invention relates generally to methods to capture, detect, analyze, screen, characterize, and quantitate antibody conjugate compounds, including antibody-drug conjugates, and their fragments and metabolites, by mass spectrometry. The invention also relates to methods to prepare mass spectrometric samples for pharmacokinetic and toxicokinetic studies.

BACKGROUND OF THE INVENTION

Antibody-drug conjugates (ADC) are targeted anti-cancer therapeutics designed to reduce nonspecific toxicities and increase efficacy relative to conventional small molecule and antibody cancer chemotherapy. They employ the powerful targeting ability of monoclonal antibodies to specifically deliver highly potent, conjugated small molecule therapeutics to a cancer cell. To evaluate properties such as pharmacokinetics and toxicity of these antibody-drug conjugates, it is useful to be able to characterize and quantitate them from plasma, urine, and other biological samples. Additionally, the ability to quantitate the free drug (not conjugated to the antibody) in the method from the same sample and the same chromatographic injection would also be useful.

A variety of mass spectrometry techniques have been employed for identification and quantitation of small molecule therapeutics in pharmacokinetic studies, such as: electron impact (EI), chemical ionization (CI), desorption chemical ionization (DCI), fast atom bombardment (FAB), electrospray ionization (ESI), matrix-assisted laser desorption/ionization (MALDI), and tandem mass spectrometry (MS/MS) (Yao et al (2001) Jour. of Chrom. B 752:9-16; Royer et al (1995) Rapid Comm. in Mass Spec. 9:495-502), including single ion monitoring (SIM) mode of ion selection for deconvolution (Souppart et al (2002) Jour. of Chrom. B 774:195-203; Wong et al (2001) Jour. of Chrom. 765:55-62; Yao et al (1998) Jour. of Chrom. B 718:77-85; Abdel-Hamid et al (2001) Jour. of Chrom. B 753:401-408; Marques et al (2001) Jour. of Chrom. 762:87-95). These methods and instrumentation require the separation of the various analytes from biological fluids for sufficient sensitivity. Such purification can be labor-intensive, slow, and require large volumes of sample fluids due to the low concentration of the analytes of interest in samples such as cell culture medium, human plasma, urine, and bile.

The direct combination of a separation/isolation/purification front-end step coupled with detection/characterization/quantitation by mass spectrometry is effective for metabolic studies of complex biological samples. Typically, LC/MS is used for characterization of antibodies (Martin et al (1997) Cancer Chemother. Pharmacol. 40:189-201; WO 03/046571; WO 03/046572), and ELISA is used for quantitation in biological matrices (Murray et al (2001) J. Imm. Methods 255: 41-56; Kirchner et al (2004) Clin. Pharmacokinetics 43(2): 83-95). ELISA assays typically are sensitive and amenable to high-throughput screens.

Recent advances in protein analysis by mass spectrometry (MS) are due to front-end gas phase ionization and introduction techniques such as electrospray ionization (ESI), matrix-assisted laser desorption ionization (MALDI, US 2003/0027216) and Surface Enhanced Laser Desorption Ionization (SELDI, U.S. Pat. No. 6,020,208), as well as improvements in instrument sensitivity, resolution, mass accuracy, bioinformatics, and software data deconvolution algorithms ("Electrospray Ionization Mass Spectrometry: Fundamentals, Instrumentation, and Applications", Cole, R. B., Ed. (1997) Wiley, New York; "Modern Protein Chemistry Practical Aspects", Howard, G. C. and Brown, W. E., Eds. (2002) CRC Press, Boca Raton, Fla., p. 71-102). The primary (sequence), secondary, and tertiary structure of proteins can be probed and elucidated with MS. Electrospray ionization (ESI) provides for the atmospheric pressure ionization (API) of a liquid sample. The electrospray process creates highly-charged droplets that, under evaporation, create ions representative of the species contained in the solution. An ion-sampling orifice of a mass spectrometer may be used to sample these gas phase ions for mass analysis. The response for an analyte measured by the mass spectrometer detector is dependent on the concentration of the analyte in the fluid and independent of the fluid flow rate.

Methods to detect and screening antibody-drug conjugates by Immunoaffinity membrane (IAM) capture and mass spectrometry have been disclosed (US 2005/0232929).

SUMMARY

An aspect of the invention includes methods to detect, screen, and quantitate antibody conjugate compounds and compositions, antibodies, and fragments and metabolites thereof, by immunoaffinity bead capture, separation, chromatography, and mass spectrometry. Exemplary methods of mass spectrometry include electrospray ionization (ESI), and full scan mass spectrometry (MS).

Immunoaffinity bead capture may be conducted with streptavidin coated paramagnetic beads capitalizing on: (i) the strong streptavidin-biotin interaction, (ii) high binding capacity to capture sufficient material for analysis of intact proteins, (iii) low non-specific binding, (iv) elution of sample constituents with mass spectrometry-compatible solvents, (v) good sample recovery, and (vi) amenability for automation.

Antibody conjugate compounds of the invention having Formula I:

wherein
Ab is an antibody;
D is a maytansinoid or monomethylauristatin drug moiety;
L is a linker covalently attached to Ab, and covalently attached to D; and
p is 1, 2, 3, 4, 5, 6, 7, or 8.

An aspect of the invention includes a method for detecting antibody-drug conjugate compounds comprising:
(i) providing an antibody-drug conjugate compound having Formula I;
(ii) contacting the antibody-drug conjugate compound, and optionally an antibody of Formula I where p is 0, or antibody fragments or metabolites thereof, with a biological source selected from a mammal, tissue, cell culture, plasma or serum;

(iii) collecting a biological sample from the biological source;

(iv) processing the biological sample to form an analysis sample by formulating, immobilizing, centrifuging, isolating, digesting, inducing or preventing blood cell clotting, hydrolyzing, or purifying to form a processed analysis sample;

(v) capturing the processed analysis sample on immunoaffinity beads comprising an antigen specific for the processed analysis sample;

(vi) eluting the processed analysis sample;

(vii) applying the eluted analysis sample to a separation media to effect separation of more than one sample constituent wherein a separated sample constituent comprises an antibody-drug conjugate compound having the Formula I, or antibody fragment or metabolite thereof, and where p is 0, 1, 2, 3, 4, 5, 6, 7, or 8; and (viii) establishing the mass to charge ratio of one or more separated sample constituents by mass spectrometry.

Another aspect of the invention includes a method for screening a mixture of antibody-drug conjugate compounds and to determine the clearance of the compounds, or fragments or metabolites thereof, in a mammal, comprising:

(i) providing a mixture of antibody-drug conjugate compounds having Formula I where the mixture optionally comprises an antibody, or fragments or metabolites thereof, where p is 0;

(ii) administering the mixture to a mammal;

(iii) collecting a blood sample or excretion from the mammal to which the mixture has been administered;

(iv) processing the blood sample or excretion to form an analysis sample by formulating, immobilizing, centrifuging, isolating, digesting, inducing or preventing blood cell clotting, hydrolyzing, or purifying to form a processed analysis sample;

(v) capturing the processed analysis sample on an immunoaffinity bead comprising an antigen specific for the processed analysis sample;

(vi) eluting the processed analysis sample;

(vii) applying the blood sample, excretion or analysis sample to a separation media to effect separation of more than one sample constituents wherein a separated sample constituent comprises an antibody-drug conjugate compound having the Formula I, or antibody fragment or metabolite thereof, and where p is 0, 1, 2, 3, 4, 5, 6, 7, or 8; and (viii) establishing the mass to charge ratio of more than one separated sample constituents by mass spectrometry.

The invention may be understood by reference to the following detailed description of the exemplary embodiments, taken in conjunction with the accompanying drawings, figures, and Examples. The discussion below is descriptive, illustrative and exemplary and is not to be taken as limiting the scope defined by any appended claims.

DETAILED DESCRIPTION OF THE EXEMPLARY EMBODIMENTS

Figure 1A:
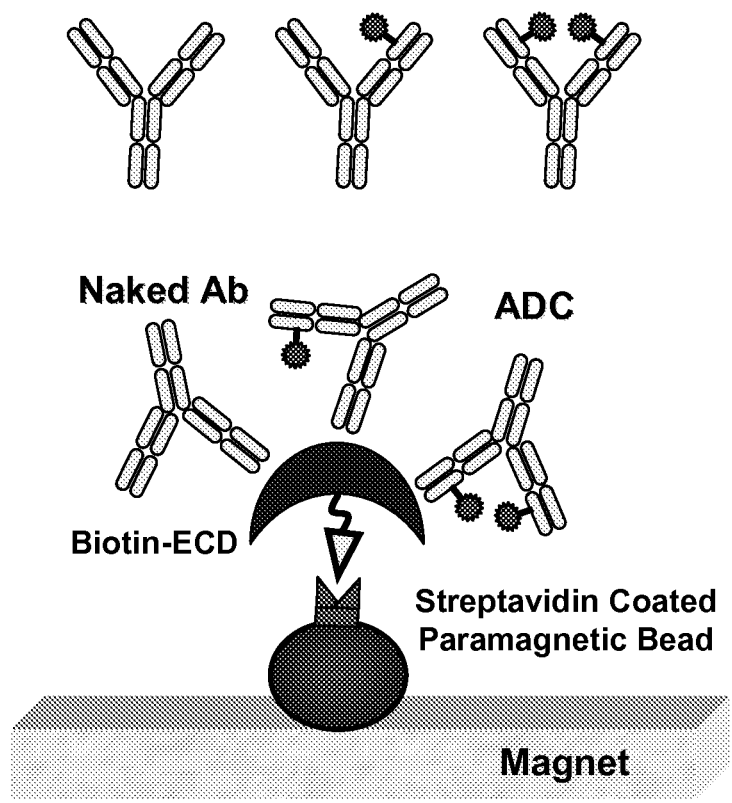
FIG. 1a shows an illustration of antibodies (MAb) and antibody-drug conjugates (ADC) binding to the ECD (extracellular domain) of a biotinylated ECD protein which is bound to a streptavidin coated paramagnetic bead in contact with a magnet.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, applicants intend to independently include the trade name product formulation, the generic drug, and the active pharmaceutical ingredient(s) of the trade name product.

Definitions

Unless stated otherwise, the following terms and phrases as used herein are intended to have the following meanings:

"Antibody" is used in the broadest sense and specifically covers monoclonal antibodies, polyclonal antibodies, multi-specific antibodies (e.g., bispecific antibodies), and antibody fragments. Antibodies may be murine, human, humanized, chimeric, or derived from other species. An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. Antibody also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

An "intact antibody" herein is one comprising a antigen-binding variable region VL and VH domains, as well as complete light and heavy chain constant domains (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA*, 81:6851-

6855). Chimeric antibodies of interest herein include "primatized" antibodies comprising variable domain antigen-binding sequences derived from a non-human primate (e.g., Old World Monkey, Ape etc) and human constant region sequences.

"Biological sample" means (i) blood, bile, urine, or feces; (ii) tissue extract; and (iii) cell culture media, cell lysate, or cell extract.

"Biological source" means (i) mammals such as a mouse, a rat, a rabbit, a dog, a monkey, or a human; (ii) mammalian tissue; and (iii) cultured cells.

"Label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Antibodies

The antibody unit (Ab-) of Formula I includes within its scope any unit of an antibody (Ab) that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the Drug unit to the particular target cell population with which the antibody unit reacts. Such antibodies include, but are not limited to, large molecular weight proteins such as, full-length antibodies and antibody fragments.

Antibodies which comprise Ab in Formula I antibody-drug conjugates (ADC) and which may be useful in the treatment of cancer include, but are not limited to, antibodies against tumor-associated antigens (TAA). Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(35) listed below. For convenience, information relating to these antigens, all of which are known in the art, is listed below and includes names, alternative names, Genbank accession numbers and primary reference(s). Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4:
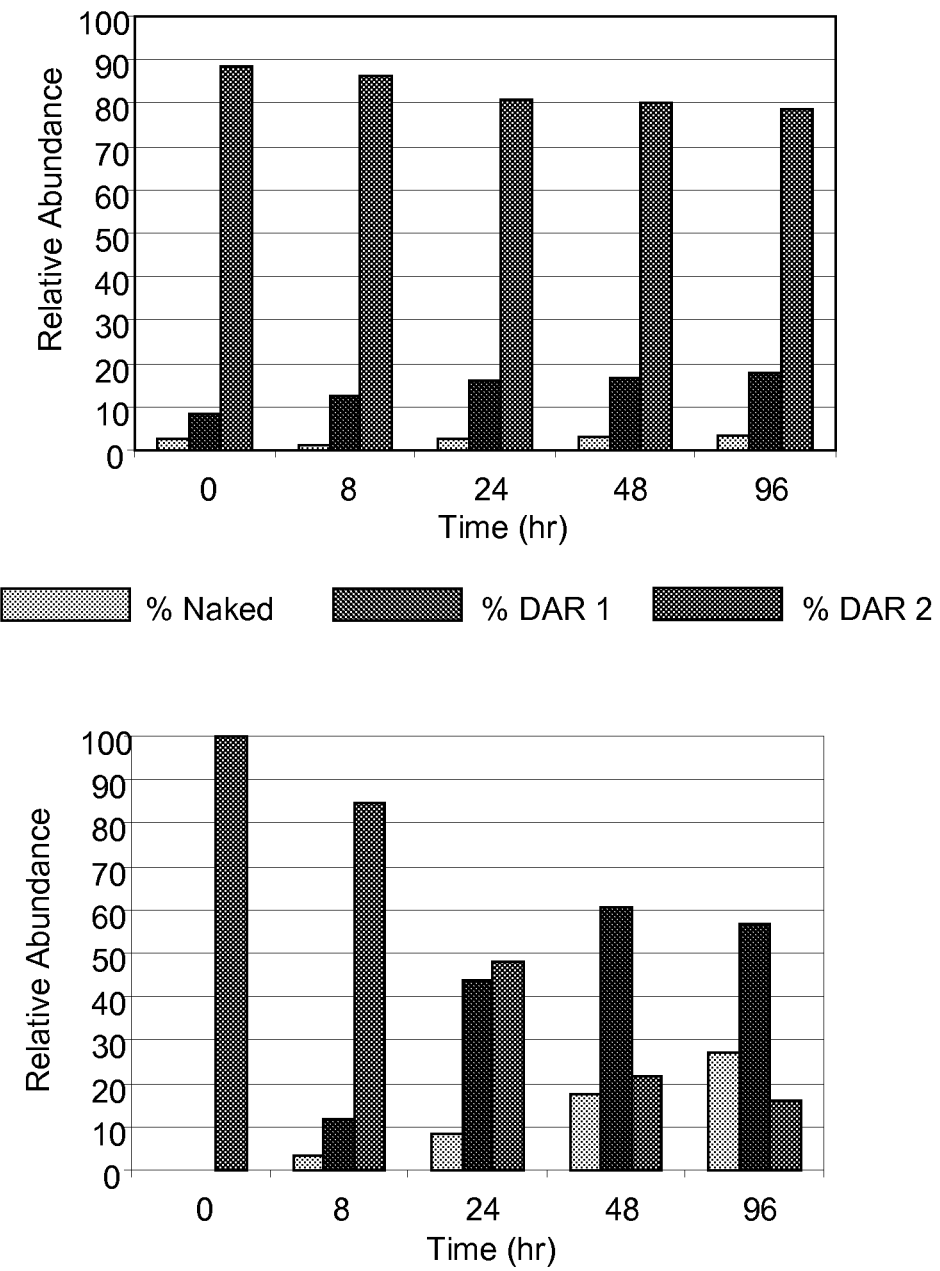
FIG. 4 shows changes in the drug/antibody ratio (DAR) distribution for: (top) light chain (Thio Hu Anti HER2 4D5 LC V205C-MC-vc-PAB-MMAE), and (bottom) heavy chain (Thio Hu Anti HER2 4D5 HC A118C-MC-vc-PAB-MMAE) ADC variants in plasma after immunoaffinity ECD modified bead capture and mass spectrometry characterization from in vitro plasma stability samples collected at 0, 8, 24, 48, and 96 hour time points. The sample constituents were assigned DAR of 0 (naked antibody), 1 (one MC-vc-PAB-MMAE drug linker unit) and 2 (two MC-vc-PAB-MMAE drug linker units).

Tumor-Associated Antigens (1)-(36):

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4). NP_001194 bone morphogenetic protein receptor, type IB/pid=NP_001194.1-Cross-references: MIM:603248; NP_001194.1; NM_001203_1

Figure 3:
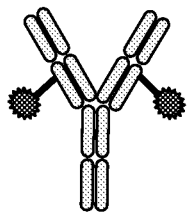
FIG. 3 shows illustrations of cysteine engineered antibody-drug conjugates, from the top to the bottom: two MMAE drug moieties located on the light chain—Thio Hu Anti HER2 4D5 LC V205C-MC-vc-PAB-MMAE; two MMAE drug moieties located on the heavy chain—Thio Hu Anti HER2 4D5 HC A118C-MC-vc-PAB-MMAE; two MMAE drug moieties located on the Fc region of the heavy chain—Thio Hu Anti HER2 4D5 Fc S400C-MC-vc-PAB-MMAE; and a cysteine engineered antibody ready for conjugation: Thio Hu Anti HER2 4D5 Fc S400C.
Figure 3:
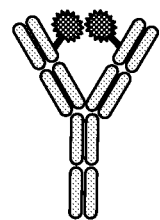
Figure 3:
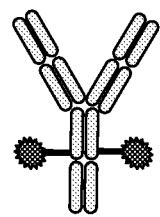
Figure 3:
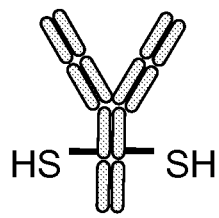

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+system), member 5/pid=NP_003477.3-*Homo sapiens*. Cross-references: MIM:600182; NP_003477.3; NM_015923; NM_003486_1

Figure 2:
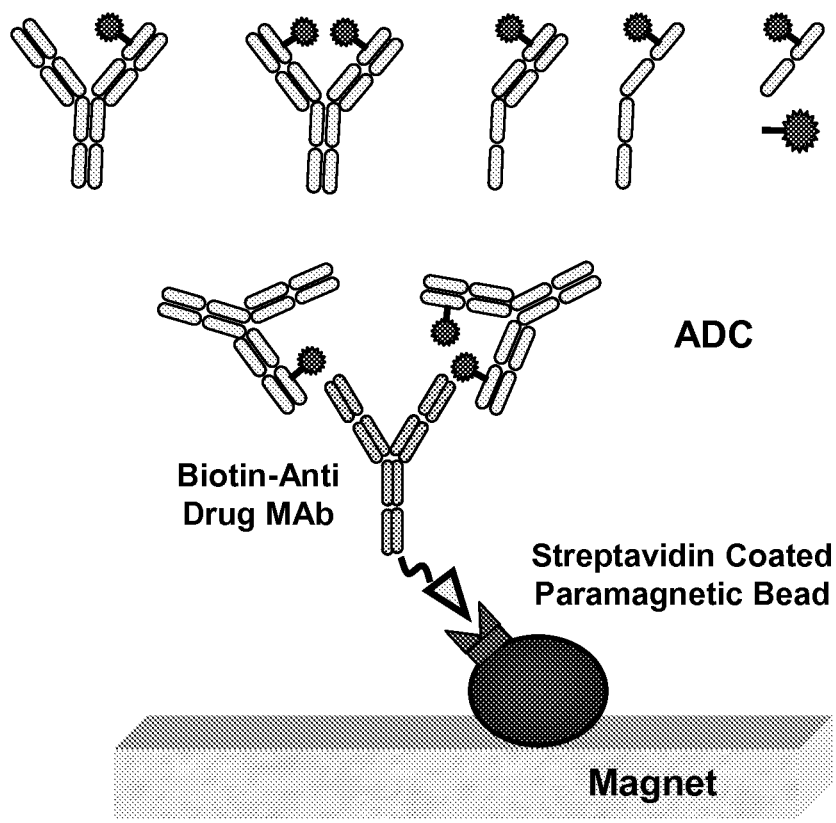
FIG. 2 shows an illustration of antibody-drug conjugates (ADC) binding to a biotinylated anti-drug monoclonal antibody (Biotin-Anti Drug MAb) which is bound to a streptavidin coated paramagnetic bead in contact with a magnet.

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate. Cross-references: MIM:604415; NP_036581.1; NM_012449_1

(4) 0772P (CA125, MUC16, Genbank accession no. AF361486) J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); US2003091580 (claim 6); WO200206317 (claim 6; Page 400-408); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999)

Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: □9P283; EMBL; AB040878; BAA95969.1. Genew; HGNC:10737;

(8) PSCA hlg (2700050C12Rik, C530008016Rik, RIKEN cDNA 2700050C12, RIKEN cDNA 2700050C12 gene, Genbank accession no. AY358628); US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1

Figure 6:
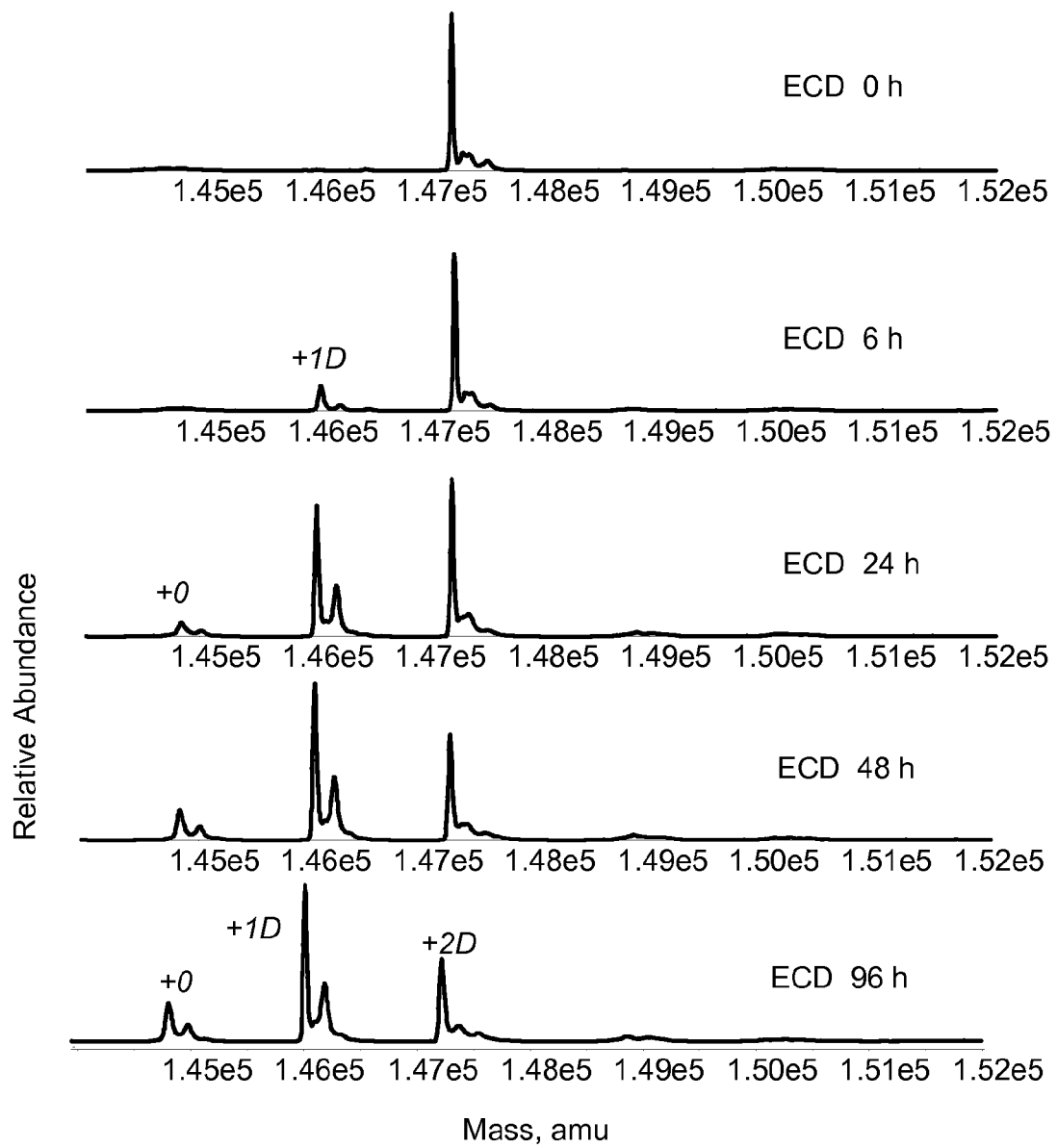
FIG. 6 shows deconvoluted mass spectrometry data of stability of Thio Hu Anti MUC16 (3A5) HC A118C-MC-vc-PAB-MMAE (100 µg/ml in rat plasma incubated at 37° C.) samples collected at 0, 6, 24, 48, and 96 hour time points. The sample constituents were assigned DAR of +0 (naked antibody), +1D (one MC-vc-PAB-MMAE drug linker unit) and +2D (two MC-vc-PAB-MMAE drug linker units).

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (claim 1a; Col 31-34); WO2004001004;

(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

Figure 9:
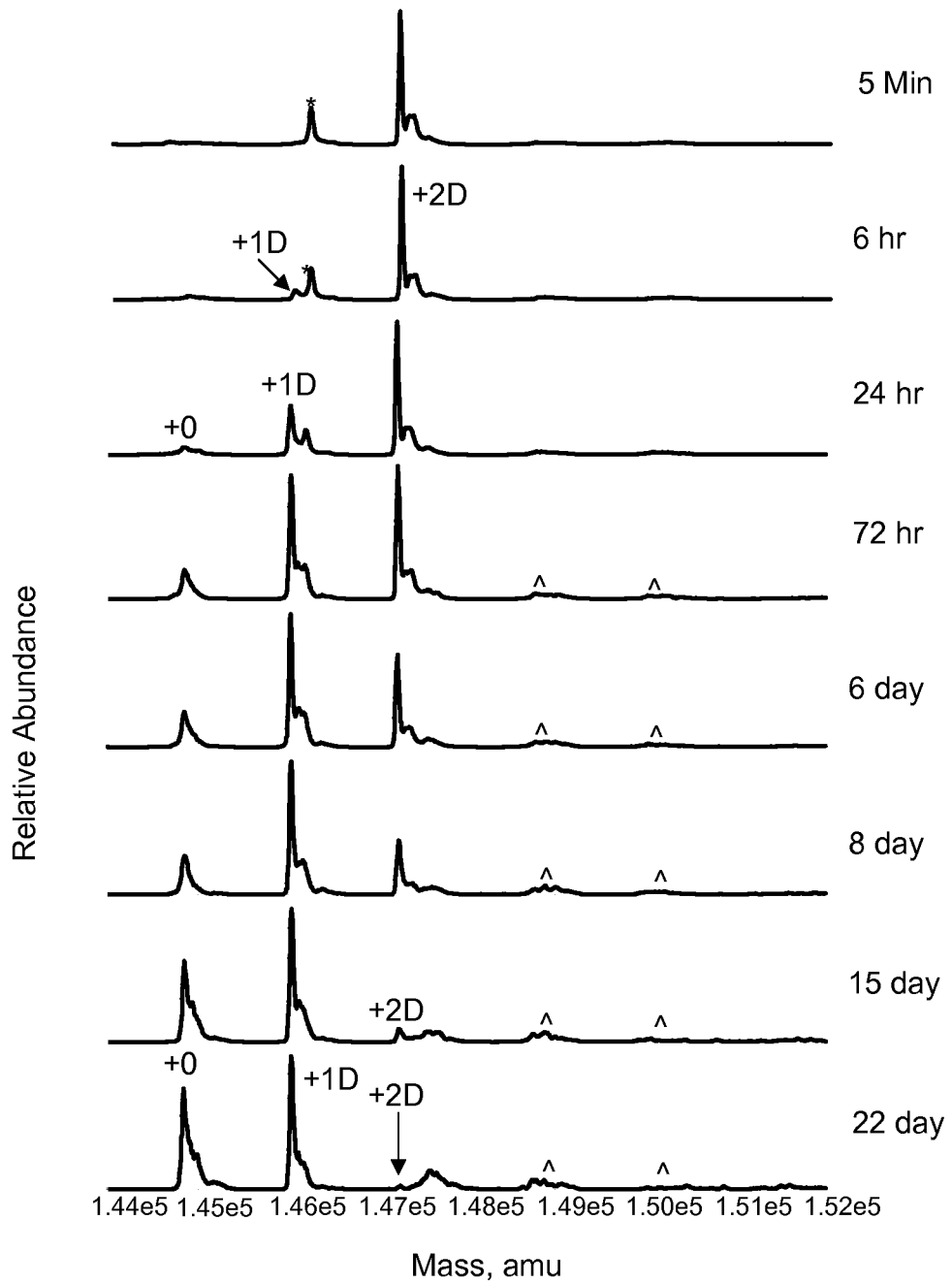
FIG. 9 shows deconvoluted mass spectrometry data of in vivo kinetics in cynomolgus monkeys dosed with 38 mg/kg Thio Hu Anti MUC16 (3A5) HC A118C-MC-vc-PAB-MMAE. The average drug loading was 1.6 MMAE/3A5. About 30% of the dosed ADC was DAR +1. Plasma samples were collected at 5 min, 6 hr, 24 hr, 72 hr, 6 day, 8 day, 15 day, and 22 day time points, and captured by immunoaffinity ECD modified bead method. The sample constituents were assigned DAR of +0 (naked antibody), +1D (one MC-vc-PAB-MMAE drug linker unit) and +2D (two MC-vc-PAB-MMAE drug linker units). The small peaks at about 149,000 and 150,000 amu are sample constituents undergoing incomplete deglycosylation.

(14) CD21 (CR2 (Complement receptor 2) or C3DR (C3d/Epstein Barr virus receptor) or Hs.73792 Genbank accession no. M26004) Fujisaku et al (1989) J. Biol. Chem. 264 (4): 2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIG. 9.1-9.9); WO2004020595 (claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674) Proc. Natl. Acad. Sci. U.S.A. (2003) 100 (7): 4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP 1B, SPAP1C, Genbank accession no. NM_030764) Genome Res. 13 (10): 2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12);

WO2003089624 (claim 25); Cross-references: MIM: 606509; NP_110391.2; NM_030764_1

Figure 1B:
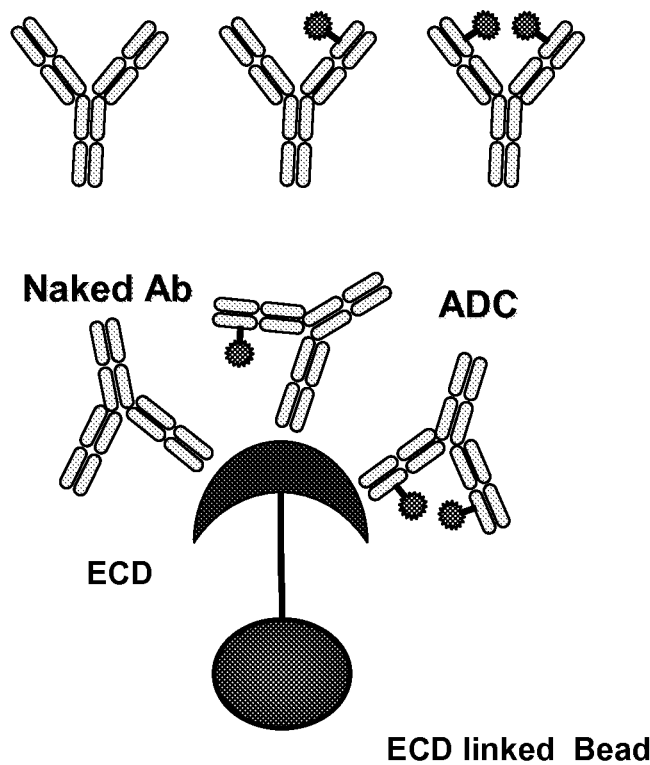
FIG. 1b shows an illustration of antibodies (MAb) and antibody-drug conjugates (ADC) binding to the ECD (extracellular domain) of an ECD protein which is covalently linked to a bead.
Figure 7:
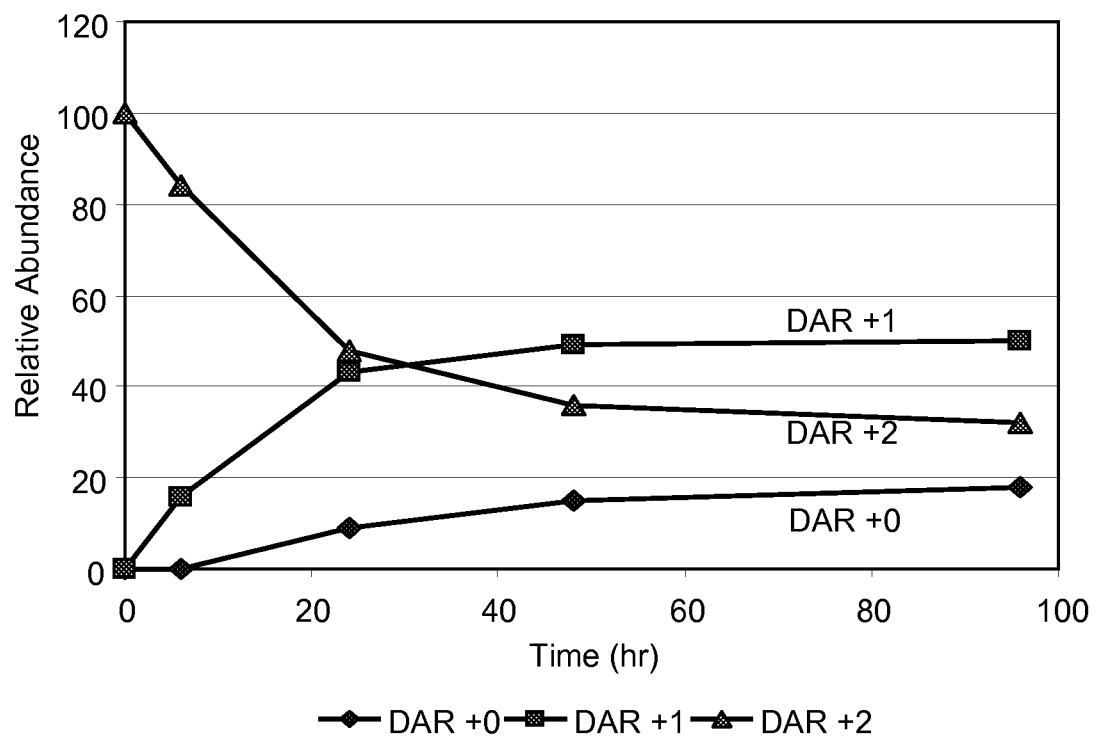
FIG. 7 shows the drug/antibody (DAR) distribution changes with time in the rat plasma stability study of Thio Hu Anti MUC16 (3A5) HC A118C-MC-vc-PAB-MMAE.
Figure 11:
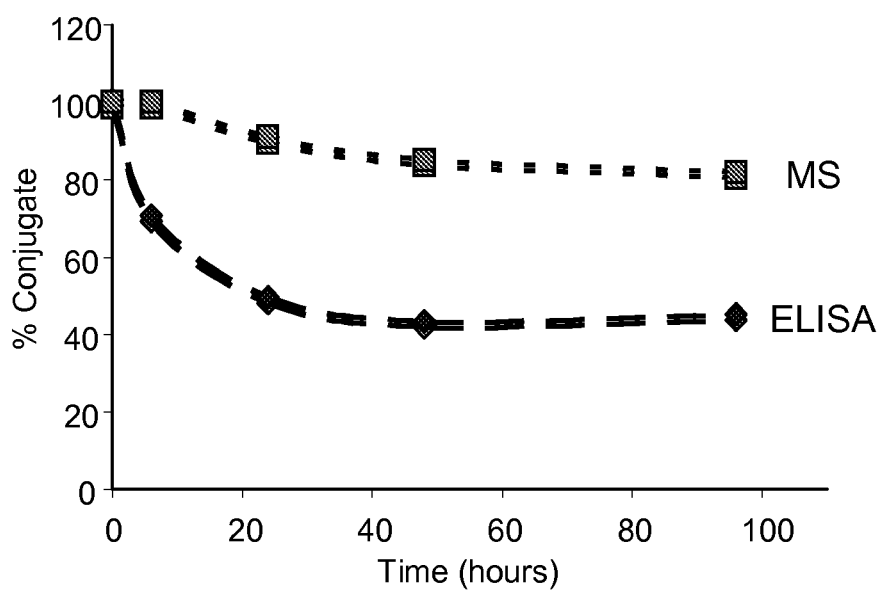
FIG. 11 shows a comparison of detection of sample constituents by the ELISA method and by the immunoaffinity ECD modified bead capture/mass spectrometry (MS) method by a plot of the percentage of antibody remaining conjugated to the drug moiety in rat plasma samples with time points up to 96 hours.

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4); Accession: P04626; EMBL; M11767; AAA35808.1. EMBL; M11761; AAA35808.1. Anti-HER2 antibodies include: HERCEPTIN® (trastuzumab, huMAb4D5-8) a full length, humanized antiHER2 (MW 145167), trastuzumab F(ab')2=derived from anti-HER2 enzymatically (MW 100,000), 4D5=full-length, murine antiHER2, from hybridoma, rhu4D5=transiently expressed, full-length humanized antibody, rhuFab4D5=recombinant humanized Fab (MW 47738), 4D5Fc8=full-length, murine antiHER2, with mutated FcRn binding domain, huMAb4D5-1, huMAb4D5-2, huMAb4D5-3, huMAb4D5-4, huMAb4D5-5, huMAb4D5-6, huMAb4D5-7 and (trastuzumab).

Figure 8:
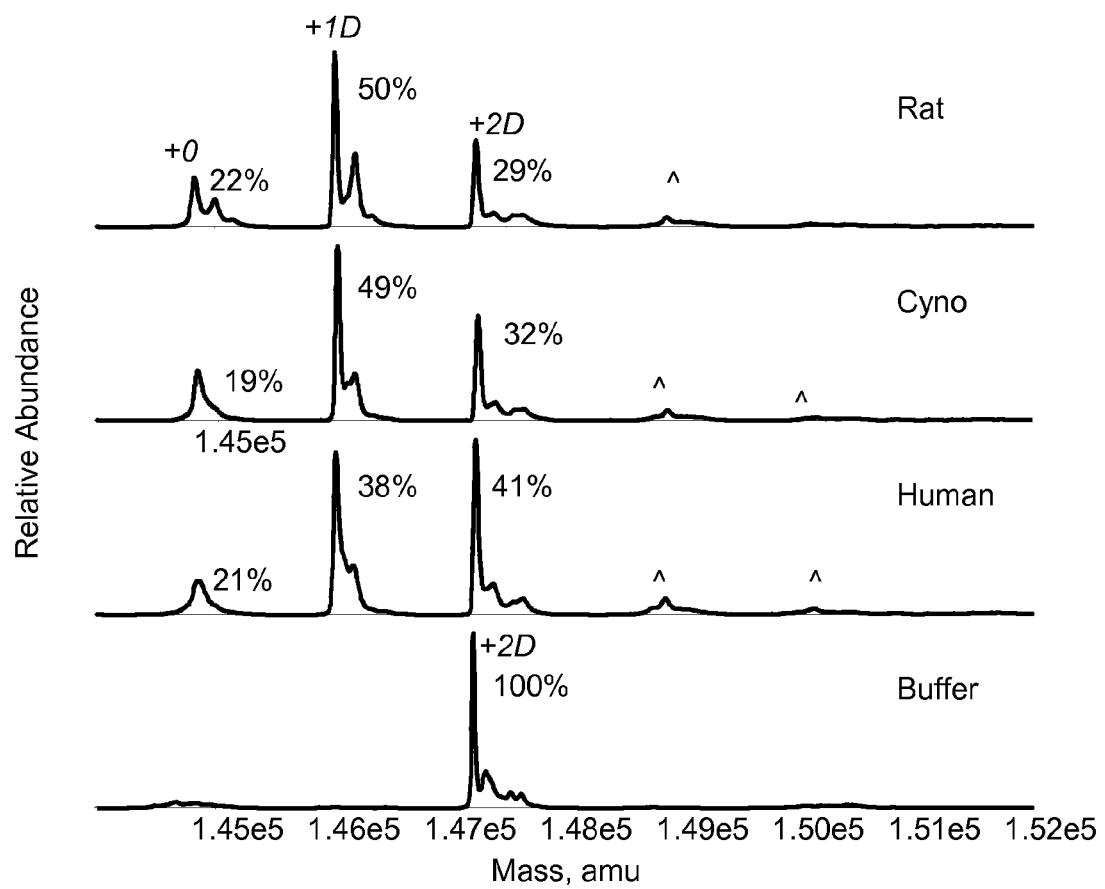
FIG. 8 shows deconvoluted mass spectrometry data of stability of Thio Hu Anti MUC16 (3A5) HC A118C-MC-vc-PAB-MMAE (100 µg/ml incubated at 37° C.) samples in rat, cynomolgus monkey, and human plasma, and Buffer (20 mM histidine/acetate, 240 mM trehalose, 0.02% polysorbate 20, pH 5.5 with 0.5% BSA) collected at the 96 hour time point and captured by rhuMUC16 ECD.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1

(23) ASLG659 (B7h, Genbank accession no. AX092328) US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1-*Homo sapiens* Species: *Homo sapiens* (human) WO2003054152 (claim 20); WO2003000842 (claim 1); WO2003023013 (Example 3, claim 20); US2003194704 (claim 45); Cross-references: GI:30102449; AAP14954.1; AY260763_1

(26) BAFF-R (B cell-activating factor receptor, BLyS receptor 3, BR3, Genbank accession No. NP_443177.1); NP_443177 BAFF receptor/pid=NP_443177.1-*Homo sapiens*; Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP-443177.1; NM_052945_1

(27) CD22 (B-cell receptor CD22-B isoform, Genbank accession No. NP-001762.1); Stamenkovic, I. and Seed, B., Nature 345 (6270), 74-77 (1990); US2003157113; US2003118592; WO2003062401 (claim 9);

WO2003072036 (claim 1; FIG. 1); WO200278524 (Example 2); Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation) PROTEIN SEQUENCE Full mpggpgv . . . dvqlekp (1.226; 226 aa), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148 (2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) PROTEIN SEQUENCE Full mnypltl . . . atslttf (1.372; 372 aa), pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+ T lymphocytes) PROTEIN SEQUENCE Full mgsgwvp . . . vllpqsc (1.273; 273 aa, pI: 6.56 MW: 30820 TM: 1 [P] Gene Chromosome: 6p21.3, Genbank accession No. NP_002111.1) Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); US6011146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) PROTEIN SEQUENCE Full mgqagck . . . lephrst (1.422; 422 aa), pI: 7.63, MW: 47206 TM: 1 [P] Gene Chromosome: 17p13.3, Genbank accession No. NP_002552.2) Le et al (1997) FEBS Lett. 418 (1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1.359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci. USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) PROTEIN SEQUENCE Full mafdvsc . . . rwkyqhi (1.661; 661 aa), pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FCRH1 (Fc receptor-like protein 1, a putative receptor for the immunoglobulin Fc domain that contains C2 type Ig-like and ITAM domains, may have a role in B-lymphocyte differentiation) PROTEIN SEQUENCE Full mlprlll . . . vdyedam (1.429; 429 aa), pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al (2001) Proc. Natl. Acad. Sci. USA 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies) PROTEIN SEQUENCE Full mllwvil . . . assaphr (1.977; 977 aa), pI: 6.88 MW: 106468 TM: 1 [P] Gene Chromosome: 1q21, Genbank accession No. NP_112571.1) WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907; CAF85723; CQ782436. WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84.

The antibody of the antibody-drug conjugates (ADC) of the invention may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. HERCEPTIN® (trastuzumab) selectively binds to the extracellular domain (ECD) of the human epidermal growth factor receptor2 protein, HER2 (ErbB2) (U.S. Pat. Nos. 5,821,337; 6,054,297; 6,407,213; 6,639,055; Coussens et al (1985) Science 230:1132-9; Slamon, et al (1989) Science 244:707-12). Trastuzumab is an IgG1 kappa antibody that contains human framework regions with the complementarity-determining regions (cdr) of a murine antibody (4D5) that binds to HER2. Trastuzumab binds to the HER2 antigen and thus inhibits the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831).

Antibodies can be labelled, or conjugated with enzymes that catalyze a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are known. The chemiluminescent substrate becomes electronically excited by a chemical reaction, such as cleavage of an O—O bond of a dioxetane group, and may then emit light which can be measured (using a chemiluminometer, for example) or donate energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example: (i) Horseradish peroxidase (HRP) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB)); (ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase. Numerous other enzyme-substrate combinations are available to those skilled in the art (U.S. Pat. Nos. 4,275,149; 4,318,980).

The label may be indirectly or non-covalently conjugated with the antibody. For example, the antibody can be conjugated with biotin and any of the categories of labels mentioned above can be conjugated with avidin, including streptavidin, or vice versa. Biotin binds selectively to avidin and thus, the label can be conjugated with the polypeptide variant in this indirect manner.

Drug Moieties

The drug moiety (D) of the Formula I antibody-drug conjugates (ADC) includes any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy. The drug moieties in the Formula I antibody-drug conjugates may have other mechanisms of action, and are not limited to any such mechanisms.

The drug moiety (D) of the antibody drug conjugates (ADC) of Formula I include maytansinoids having the structure:

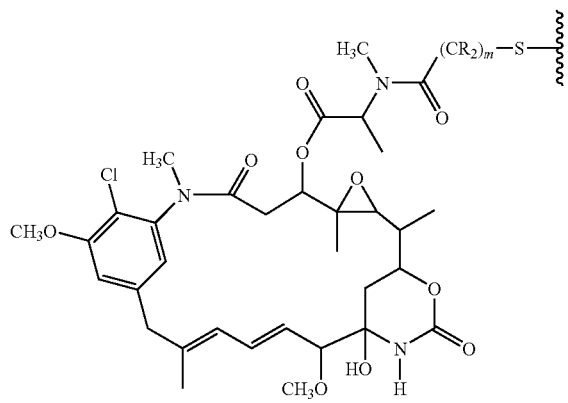

where the wavy line indicates the covalent attachment of the sulfur atom of D to a linker (L) of an antibody drug conjugate (ADC). R may independently be H or a $C_1$-$C_6$ alkyl. The alkylene chain attaching the amide group to the sulfur atom may be methyl, ethyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine was isolated from the east African shrub *Maytenus serrata* and shown to be 100- to 1000-fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al., (1978) J. Med. Chem. 21:31-37; Higashide et al. (1977) Nature 270:721-722; Kawai et al., 32 Chem. Pharm. (1984) Bull. 3441-3451). Analogs of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4, 5. The naturally occurring and synthetic C-3 esters can be classified into two groups: (a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230 and 4,260,608; and Kawai et al., (1984) Chem. Pharm. Bull. 32:3441-3451). Esters of group (b) were found to be much more cytotoxic than esters of group (a).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

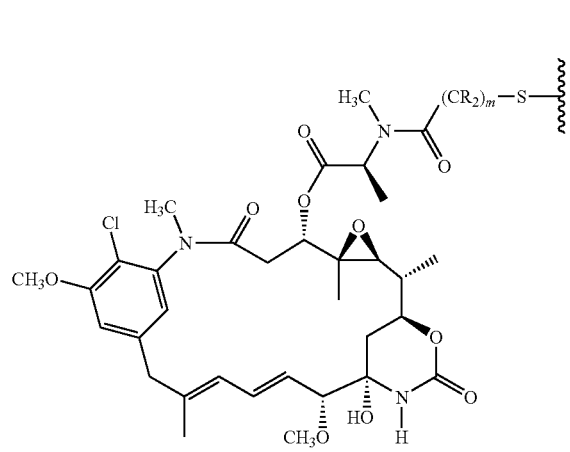

Exemplary embodiments of maytansinoid drug moieties include: DM1, $(CR_2)_m$=$CH_2CH_2$; DM3, $(CR_2)_m$=$CH_2CH_2CH(CH_3)$; and DM4, $(CR_2)_m$=$CH_2CH_2C(CH_3)_2$, having the structures:

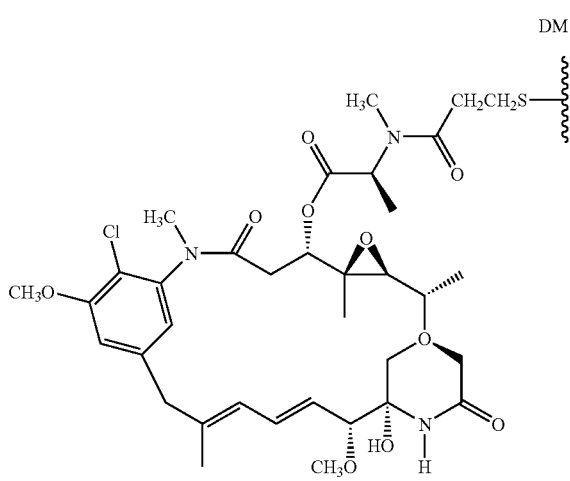

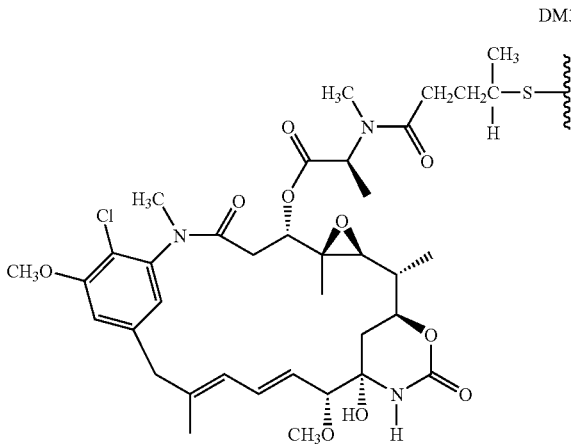

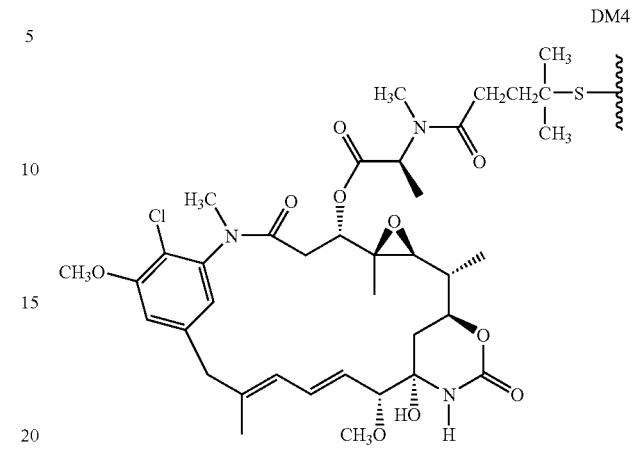

The drug moiety (D) of the antibody drug conjugates (ADC) of Formula I also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The auristatin peptides, auristatin E (AE) and monomethylauristatin (MMAE), synthetic analogs of dolastatin (WO 02/088172), have been conjugated as drug moieties to: (i) chimeric monoclonal antibodies cBR96 (specific to Lewis Y on carcinomas); (ii) cAC 10 which is specific to CD30 on hematological malignancies (Klussman, et al (2004) Bioconjugate Chemistry 15(4):765-773; Doronina et al (2003) Nature Biotechnology 21(7):778-784; Francisco et al (2003) Blood 102(4):1458-1465; US 2004/0018194; (iii) anti-CD20 antibodies such as rituxan (WO 04/032828) for the treatment of CD20-expressing cancers and immune disorders; (iv) anti-EphB2R antibody 2H9 for treatment of colorectal cancer (Mao et al (2004) Cancer Research 64(3):781-788); (v) E-selectin antibody (Bhaskar et al (2003) Cancer Res. 63:6387-6394); (vi) trastuzumab (HERCEPTIN®, US 2005/0238649), and (vi) anti-CD30 antibodies (WO 03/043583). Variants of auristatin E are disclosed in U.S. Pat. Nos. 5,767,237 and 6,124,431, including monomethylauristatin E conjugated to monoclonal antibodies (Senter et al, Proceedings of the American Association for Cancer Research, Volume 45, Abstract Number 623, presented Mar. 28, 2004). Auristatin analogs MMAE and MMAF have been conjugated to various antibodies (US 2005/0238649).

The monomethylauristatin drug moiety (D) of the antibody-drug conjugates (ADC) of Formula I include the auristatin drug moieties MMAE (U.S. Pat. No. 7,090,843) and MMAF (US 2005/0238649). The N-terminus of the MMAE or MMAF drug moiety is covalently attached via a linker to a engineered cysteine of the antibody.

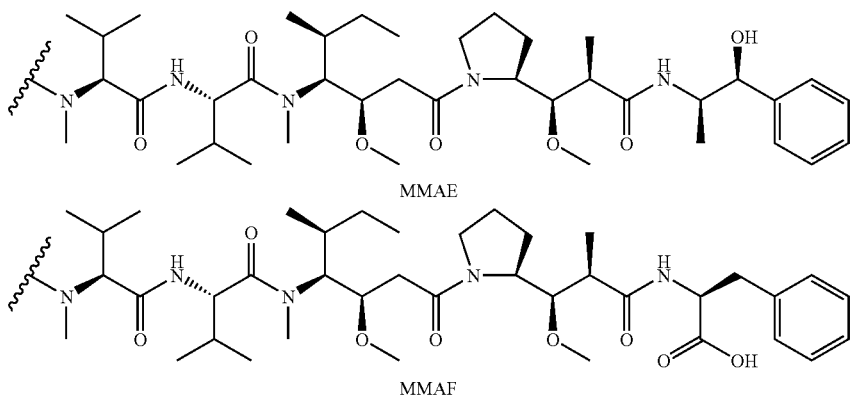

MMAE

MMAF

Other exemplary auristatin drug moieties include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Linkers

A linker is a bifunctional or multifunctional chemical moiety comprising a covalent bond or a chain of atoms that covalently attaches an antibody (Ab) to a drug moiety (D) according to Formula I antibody-drug conjugates. Antibody-drug conjugates (ADC) can be conveniently prepared using a Linker (L) having reactive functionality for binding to the Drug and to the Antibody. A Linker may have an electrophilic group reactive with a nucleophilic group present on an antibody, such as thiol or amino. A cysteine thiol of the antibody is reactive with an electrophilic group on a Linker and forms a covalent bond to a Linker. Useful electrophilic groups include, but are not limited to, maleimide and haloacetamide groups. Linkers also include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. Useful nucleophilic groups on an antibody include but are not limited to, sulfhydryl, hydroxyl and amino groups.

In another embodiment, a linker reagent or drug-linker reagent has a reactive nucleophilic functional group which is reactive with an electrophile present on an antibody to form a covalent bond. Useful electrophilic groups on an antibody include, but are not limited to, aldehyde and ketone carbonyl groups. Useful nucleophilic groups on a linker include, but are not limited to, hydrazide, oxime, amino, hydrazine, thiosemicarbazone, hydrazine carboxylate, and arylhydrazide.

The linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), N-succinimidyl 4-(2-pyridylthio) pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy —$CH_2CH_2O$— as one or more repeating units ("EO" or "PEO"). Additional linker components are known in the art and some are described herein.

In one embodiment, the antibody has one or more lysine residues that can be chemically modified to introduce one or more sulfhydryl groups. The antibody unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the antibody can have one or more carbohydrate groups that can be chemically modified to have one or more sulfhydryl groups. The antibody unit bonds to the linker, such as the Stretcher Unit, via the sulfhydryl group's sulfur atom. In yet another embodiment, the antibody can have one or more carbohydrate groups that can be oxidized to provide an aldehyde (—CHO) group (see for example, Laguzza, et al (1989) J. Med. Chem. 32(3):548-55). The corresponding aldehyde can form a bond with a Reactive Site on a Stretcher. Reactive sites on a Stretcher that can react with a carbonyl group on an antibody include, but are not limited to, hydrazine and hydroxylamine. Other protocols for the modification of proteins for the attachment or association of Drug Units are described in Coligan et al., "Current Protocols in Protein Science", vol. 2, John Wiley & Sons (2002), incorporated herein by reference.

In another embodiment, the linker may be substituted with groups which modulated solubility or reactivity. For example, a charged substituent such as sulfonate (—$SO_3^-$) or ammonium, may increase water solubility of the reagent and facilitate the coupling reaction of the linker reagent with the antibody or the drug moiety, or facilitate the coupling reaction of Ab-L (antibody-linker) with D, or D-L (drug linker reagent) with Ab, depending on the synthetic route employed to prepare the ADC.

The compounds of the invention expressly contemplate, but are not limited to, ADC prepared with cross-linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_2$, and BM(PEO)$_3$, which are commercially available from Pierce Biotechnology, Inc. Bis-maleimide reagents allow the attachment of the thiol group of a cysteine residue of an antibody to a thiol-containing drug moiety, label, or linker intermediate, in a sequential or concurrent fashion. Other functional groups besides maleimide, which are reactive with a thiol group of an antibody, drug moiety, label, or linker intermediate include iodoacetamide, bromoacetamide, vinyl pyridine, disulfide, pyridyl disulfide, isocyanate, and isothiocyanate. Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

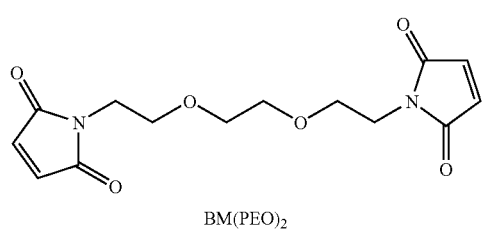

BM(PEO)$_2$

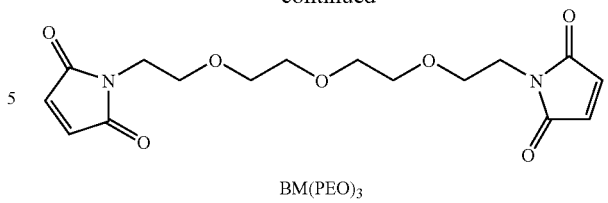

BM(PEO)$_3$

Reactive thiol groups of cysteine engineered antibodies (US 2007/0092940) react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773.

Antibody Drug Conjugates

Embodiments of Formula I ADC include monomethylauristatin drug moieties (D) MMAE and MMAF, and linkers comprising maleimidocaproyl (MC), valine-citrulline (vc), and para-aminobenzylcarbamoyl (PAB) subunits), as disclosed in US 2005/0238649. Exemplary ADC include:

Ab-MC-vc-PAB-MMAF:

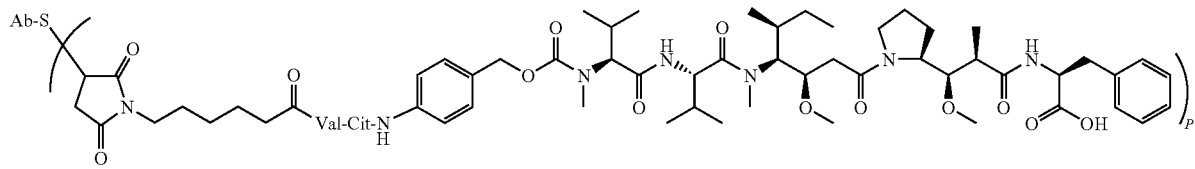

Ab-MC-vc-PAB-MMAE:

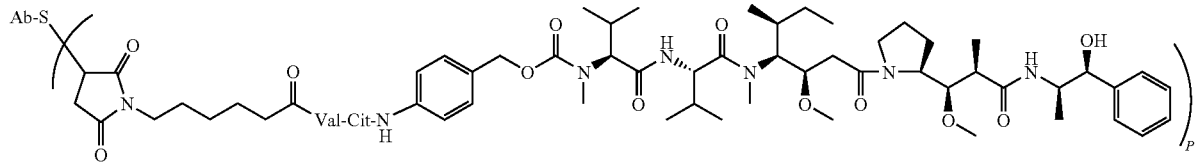

Ab-MC-MMAE:

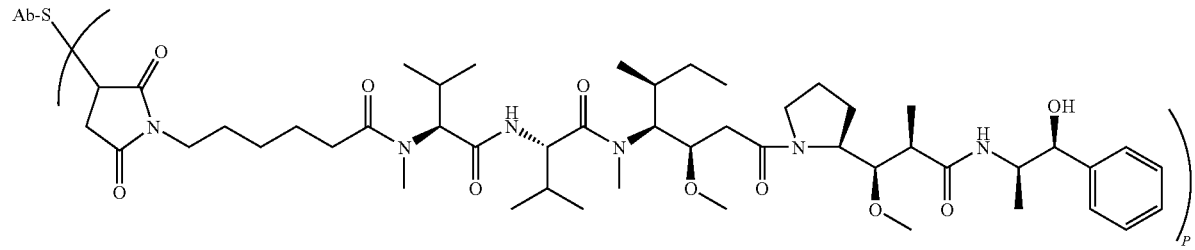

Ab-MC-MMAF:

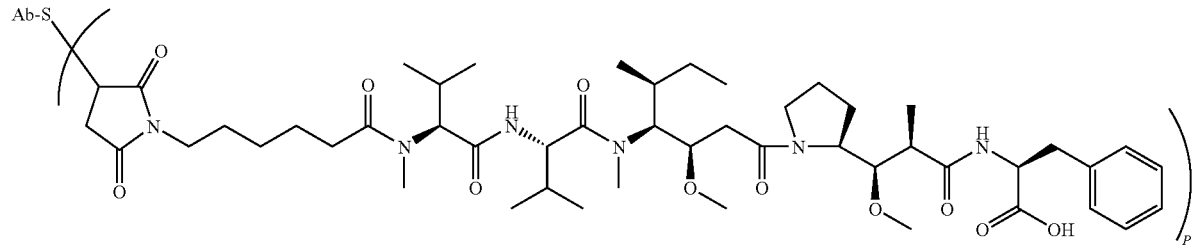

The above exemplary monomethylauristatin ADC may be prepared from an antibody with a reactive cysteine thiol group, such as a cysteine engineered antibody (US 2007/0092940) and drug linker reagents MC-val-cit-PAB-MMAF, MC-val-cit-PAB-MMAE, MC-MMAF, and MC-MMAE, respectively (Doronina et al (2003) Nature Biotechnology 21(7):778-784; Francisco et al (2003) Blood 102:1458-1465; US 2005/0238649).

Specific embodiments of cysteine engineered antibodies and corresponding ADC are shown in FIG. 3, from the top to the bottom: two MMAE drug moieties located on the light chain—Thio Hu Anti HER2 4D5 LC V205C-MC-vc-PAB-MMAE; two MMAE drug moieties located on the heavy chain—Thio Hu Anti HER2 4D5 HC A118C-MC-vc-PAB-MMAE; two MMAE drug moieties located on the Fc region of the heavy chain—Thio Hu Anti HER2 4D5 Fc S400C-MC-vc-PAB-MMAE; Thio Hu Anti HER2 4D5 Fc S400C; and a cysteine engineered antibody ready for conjugation: Thio Hu Anti HER2 4D5 Fc S400C. Cysteine engineered antibodies are designed and selected according to US 2007/0092940.

Embodiments of Formula I ADC include maytansinoid drug moieties (D) DM1, DM3, and DM4, and linkers formed from linker reagents such as SPP, SPDB, and SMCC, as disclosed in US 2005/0276812. Exemplary antibody-drug conjugates include Ab-SPP-DM1:

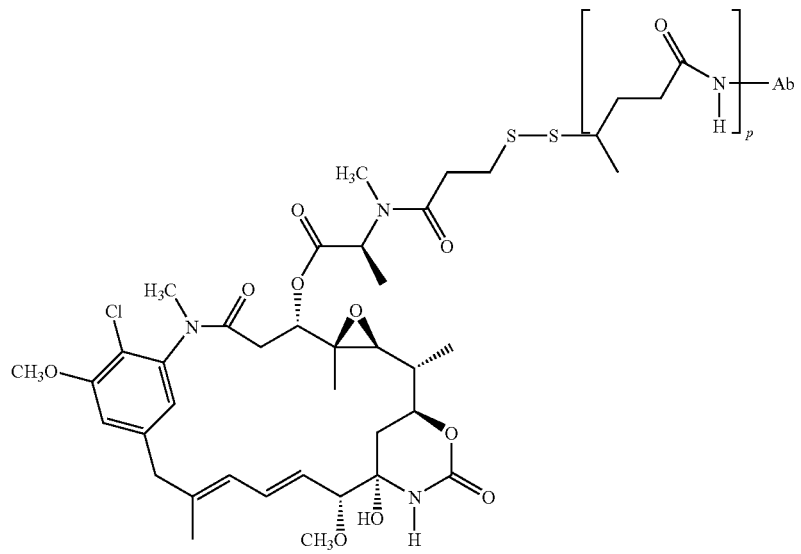

Ab-SMCC-DM1:

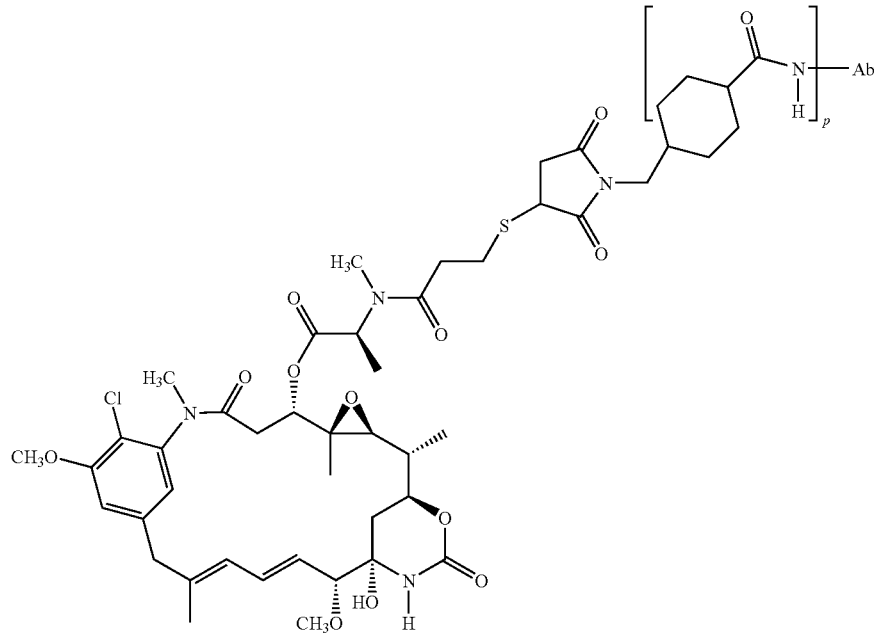

Exemplary antibody drug conjugates where DM1 is linked through a BMPEO linker to a thiol group of an antibody have the structure:

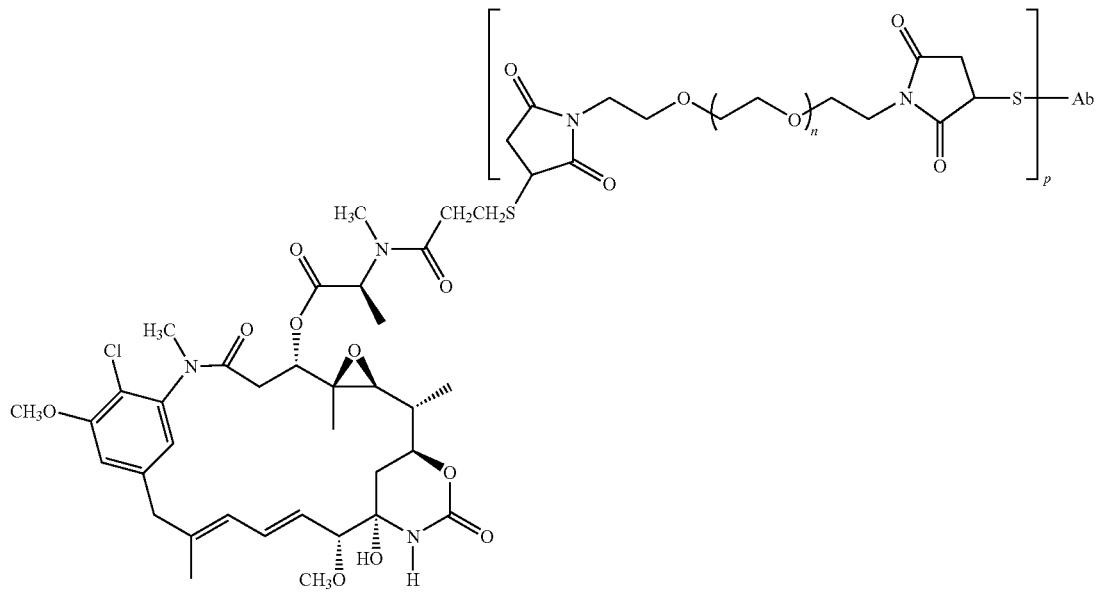

where n is 0, 1, or 2; and p is 1, 2, 3, or 4.

Drug Loading

The drug loading value is represented by p, the number of drug moieties per antibody in a molecule of Formula I. Compositions of ADC of Formula I include mixtures of antibodies conjugated with a range of drugs, from 1 to about 8. The mixtures of antibody-drug conjugates resulting from conjugation of an antibody and a drug-linker reagent, or from conjugation of an antibody-linker with a drug reagent, may be characterized as having an average drug loading value of about 1 to about 8, depending on the conjugation conditions. Each preparation of an ADC by conjugation of an antibody to a drug moiety results in a potential distribution of product molecules, bearing one or more drugs bound to antibody, or where the antibody has not been linked to a drug moiety, where p=0. The average number of drugs per antibody in preparations of ADC from conjugation reactions may be characterized by the methods of the present invention, i.e. affinity mass spectrometry, and by ELISA assay. By ELISA, the averaged value of p in a particular preparation of ADC may be determined (Hamblett et al (2004) Clinical Cancer Res. 10:7063-7070; Sanderson et al (2005) Clinical Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. This important distribution parameter may be determined by methods of the present invention with the separation of the individual molecules of an ADC composition and their characterization and quantitation. Separation of the constituents of the sample occurs both at the separation media step of the method and during the mass spectrometry step. The high selectivity of the separation media step of the methods of the invention provides separation and purification of individual ADC constituents from complex, heterogeneous biological samples. The high resolution and accuracy of the mass spectrometric step of the methods of the invention provides detection and quantitation of the separated ADC constituents.

The methods of the invention can determine the amount of bound drug per antibody (loading) of ADC and the distribution of drug moieties on fragments such as heavy chain and light chain, and even to locate covalently attached drug moieties in sub-fragment loci of the antibody, or at particular amino acid residues.

For some ADC, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. Less reactive amino acid residues such as lysine may be more numerous in the antibody to be conjugated, but may be unreactive and unavailable for reaction with the drug moiety or drug-linker reagent. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges and must be reduced with a reducing agent such as dithiothreitol (DTT) or tris(2-carboxyethyl)phosphine hydrochloride (TCEP), under partial or total reducing conditions. Additionally, the antibody may be subjected to denaturing, or partially denaturing, conditions to reveal reactive nucleophilic groups such as lysine or cysteine. The loading (drug/antibody ratio) of an ADC may be controlled by several parameters, including: (i) limiting the molar excess of drug-linker intermediate or linker reagent relative to antibody, (ii)

limiting the conjugation reaction time or temperature, and (iii) partial or limiting reductive conditions for cysteine thiol modification.

Where more than one nucleophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). However, these single loading value ADCs may still be heterogeneous mixtures because the drug moieties may be attached, via the linker, at different sites on the antibody.

Administration of Antibody Drug Conjugates

The antibody drug conjugates (ADC) of the invention may be contacted with, or administered to, biological sources by any route appropriate to the condition to be treated. The ADC will typically be administered to a mammal parenterally, i.e. infusion, subcutaneous, intramuscular, intravenous, intradermal, intrathecal and epidural. The biological sources that may be contacted, i.e. administered, with Formula I ADC, include: (i) mammals such as a mouse, a rat, a rabbit, a dog, a monkey, or a human; (ii) mammalian tissue; and (iii) cultured cells. Biological samples are collected from the biological source once, or at timed, periodic, or random intervals. Biological samples include: (i) blood, bile, urine, or feces; (ii) tissue extracts; and (iii) cell culture media, cell lysates, or cell extracts.

The affinity capture LC-MS methods of the invention may be employed in tissue analysis to determine the mechanism of toxicity of antibody-drug conjugate compounds.

Pharmaceutical Formulations

Pharmaceutical formulations of therapeutic antibody drug conjugates (ADC) of the invention are typically prepared for parenteral administration, i.e. bolus, intraveneous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to biological source recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including guar gum and dextrins; sugars such as glucose, mannose, sucrose, mannitol, trehalose or sorbitol; chelating agents such as EDTA; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Metabolites of the Antibody Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically may be identified by administering the antibody-drug conjugate mixture in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its metabolized products from processing the urine, blood or other biological samples. The metabolite structures are determined by the mass spectrometric methods of the invention.

Pharmacokinetics

Monitoring circulating levels of a therapeutic for pharmacokinetic (PK) determinations in a mammal, including half-life, clearance, area under the curve (AUC), and volume of distribution, is necessary to establish safety/toxicity limits and appropriate dosing regimen (Welling, P. (1997) Pharmacokinetics Processes, Mathematics, and Applications, 2nd Ed., American Chemical Society, Washington, D.C.). Bioavailability is the extent to which the administered compound reaches general circulation from the administered dose form, usually expressed as a percentage of the administered dose. The half-life of a compound is the time required for 50% of the peak plasma concentration of the compound to be removed by excretion or biotransformation (metabolism). The therapeutic index expresses the selectivity of the compound between the desired therapeutic activity and the undesired toxic side effects. The pharmacokinetic measurements from the methods of the invention elucidate the absorption, distribution, metabolism, and excretion (ADME) of antibodies and antibody-drug conjugates (ADC).

When administered in vivo, the antibody-drug conjugate may undergo hydrolysis, drug moiety cleavage, antibody denaturation, glucuronidation, oxidation, or other metabolic degradation events. The bead-based affinity capture and mass spectrometry methods of the invention are developed to accurately characterize and measure the products of these events.

Processing Biological Samples

An antibody-drug conjugate (ADC) compound of Formula I, and optionally an antibody of Formula I where p is 0, or antibody fragments or metabolites thereof, is administered to, or contacted with, a biological source selected from a mammal, tissue, cell culture, plasma or serum. Analysis from serum and plasma samples is known to be problematic due to their high proteomic background, i.e. many proteins and other analytes. After a certain period of time, ranging from minutes, hours, days, a biological sample comprising the antibody-drug conjugate compound having the Formula I, or fragment or metabolite thereof is collected. The biological sample may be collected by any means, including withdrawing a fluid by syringe or cannula. The biological sample may be blood or blood products such as serum, plasma or the like, cerebrospinal fluid or other body fluid, e.g. saliva, urine, lymph, bile, feces, sweat, or breath vapor.

The biological samples are processed to form analysis samples by conventional procedures including: formulating, immobilizing, centrifugation, isolating, digesting, inducing or preventing blood cell clotting, hydrolyzing, or purifying.

Processing biological samples serves to remove impurities and reduce sample heterogeneity which may hinder separation of the sample constituents, or obscure data collection or analysis. Alternatively, or in addition to, processing simplifies sample handling, preserves from degradation, minimizes sample volume, or selects for the sample constituents (analytes) of interest in the mass spectrometric analysis. Alternatively, or in addition to, processing converts biological samples into metabolites, fragments, or derivatives which are of interest in determining drug metabolism or pharmacokinetic effects.

Capturing Processed Analysis Samples

The antibody-drug conjugate (ADC) compound of Formula I, and optionally an antibody of Formula I where p is 0, or antibody fragments or metabolites thereof are captured on immunoaffinity beads where the beads have an immobilized antigen specific for the antibody or drug of the ADC. An antigen specific for the antibody of the administered antibody-drug conjugate is biotinylated and bound to streptavidin coated paramagnetic beads through strong biotin-streptavidin interaction ($K_D=10^{-15}$ M). FIG. 1a illustrates one embodiment referred to as ECD capture. Antibodies (MAb) and antibody-drug conjugates (ADC) bind to the ECD (extracellular domain) of a biotinylated ECD protein which is bound to a streptavidin coated paramagnetic bead in contact with a magnet. FIG. 1b illustrates another embodiment of ECD capture where antibodies (MAb) and antibody-drug conjugates (ADC) bind to the ECD (extracellular domain) of an ECD protein which is covalently attached to a bead. The bead may be configured in a column format or loose in a well. FIG. 2 illustrates another embodiment of anti-drug moiety antibody capture where antibody-drug conjugates (ADC) bind to a biotinylated anti-drug monoclonal antibody (Biotin-Anti Drug MAb) which is bound to a streptavidin coated paramagnetic bead in contact with a magnet.

The immunoaffinity bead may comprise a porous polymer monolith and may be configured in a flow-through channel in fluid communication with a collection reservoir. The beads may be contained in a flow-through vessel, such as a column or funnel wherein the sample from the biological source is introduced at one end or orifice, and a sample is eluted from another end or orifice. The immunoaffinity beads may be distributed in a plurality of flow-through vessels, each in communication with a separate collection reservoir. The vessels and reservoirs may be configured in a 96 microtitre well format of 12×8 columns and rows, or a 384 microtitre well format of 24×16 columns and rows for purposes of automation and reproducibility of results.

Plasma or serum samples from the mammal (biological source) that received the antibody-drug conjugate composition are applied to the beads by manual pipetting or automated robotic dispensing. The beads may be configured in a well or other vessel, or configured in a column, or other flow-through device where the sample is introduced at one end or orifice, and wash effluent or eluted sample is eluted from another end or orifice. Sample constituents specific for the bead bound antigen are allowed to bind. The beads are washed to rinse off non-specific proteins and other non-specific sample constituents. Bound antibodies may be deglycosylated on the beads, e.g. with PNGaseF. The bound sample constituents may be eluted into a sample plate, with segregated receiving vessels or wells. The eluted samples may then be addressed by manual pipetting or by robotic transfer and separated by reverse phase chromatography and the separated sample constituents are analyzed by mass spectrometry.

Rationale for using streptavidin coated paramagnetic beads includes: (i) the strong streptavidin-biotin interaction ($K_D=10^{-15}$ M), (ii) the immobilized streptavidin/biotinylated analyte is a proven method, (iii) the high binding capacity (sufficient material for intact proteins), (iv) low non-specific binding, (v) elution of sample with mass spectrometry-compatible solvents, (vi) good sample recovery from beads, and (vii) ease of use and amenable for automation In an exemplary embodiment, the biological sample may be digested with trypsin digestion. For trypsin digestion, samples may be reduced with DTT, S-carboxymethylated with sodium iodoacetate, and then digested with trypsin. Digested samples may be analyzed by: (i) reverse phase HPLC, e.g. Nucleosil C18 column; (ii) size-exclusion chromatography (SEC), e.g. TSK 3000SWxL column; or (iii) boronate affinity chromatography using a TSK Boronate column.

Separation of Sample Constituents

To form the analysis sample, the biological sample may be applied to a separation media to effect separation of more than one sample constituent. Separation methods include affinity, chromatography, and electrophoresis methods. Affinity methods include affinity chromatography, adsorption, and immobilized affinity matrices. Chromatography methods include HPLC, hydrophobic interaction (HIC), anion exchange, cation exchange, reverse-phase, normal phase, ion-pair reverse-phase, thin-layer, capillary flow, and size-exclusion. Electrophoretic methods include single dimensional, slab gel, capillary, polyacrylamide, denaturing, native, free solution, paper, 2-dimensional, isoelectric focusing, and gradient voltage. Other separation methods include: dialysis, centrifugation, sedimentation, floatation, precipitation, immunoprecipitation, and gel filtration.

Separation methods may effect separation of the constituents of the biological sample by one or more physico-chemical properties including, but not limited to, elution time, hydrophobicity, hydrophilicity, migration time, rate, velocity, chromatographic retention time, solubility, molecular volume or size, net charge, charge state, ionic charge, isoelectric point, dissociation constant (pKa), antibody affinity, electrophoretic mobility, ionization potential, dipole moment, hydrogen-bonding capability, and ion mobility in gas phase.

Low rate of flow by capillary flow infusion into the mass spectrometry inlet device facilitates sensitivity of mass detection, allowing for lower concentration analytes and higher molecular weight species such as intact proteins and antibody-drug conjugates to be detected and characterized.

Mass Spectrometry of Separated Sample Constituents

Preparation of Antibody-Drug Conjugate Samples for Mass Spectrometric analysis can be conducted generally according to known techniques. See: "Modern Protein Chemistry: Practical Aspects", Howard, G. C. and Brown, W. E., Eds. (2002) CRC Press, Boca Raton, Florida.

The methods of the invention are appropriate for the analysis of antibody mixtures derived from biological samples where different chemical constituents of the mixture are first isolated, separated, or partially separated by one or more processes including affinity or chromatography which cause the constituents to elute sequentially or in a batch wise manner, or to be directly detected by mass spectrometry. Various structural features and properties of antibodies can be elucidated from mass spectrometry analysis including: fragmentation, deamidation, glycation, oxidation, partial sequence information, e.g. N-terminal and C-terminal, dimer and aggregation states. One or more chemical constituents in the biological sample can be characterized in a highly specific manner by measurement of its accurate mass since the administered antibody-drug conjugate is of known sequence, structure, and molecular weight.

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and atmospheric pressure chemical ionization (APCI) and Matrix Assisted Laser Desorption Ionization (MALDI). ESI and MALDI are the two most commonly employed methods to ionize proteins for mass spectrometric analysis. ESI and APCI are the most commonly used ion source techniques for analysis of small molecules by LC/MS (Lee, M. "LC/MS Applications in Drug Development" (2002) J. Wiley & Sons, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing multiple reactive moieties at different sites on a substrate surface, throughput may be increased.

In functional systems, the mass spectrometer will accurately measure the mass of a chemical species of interest to within 20 ppm of its exact or calculated mass, and typically within 5 ppm or less of its exact or calculated mass. Commercially available mass analyzers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

Electrospray Ionization Mass Spectrometry (ESI)

Higher sensitivity is achieved at lower flow rates due to increased analyte ionization efficiency (Gale et al (1993) Rapid Commun. Mass Spectrom. 7:1017). Thus by performing electrospray injection of a sample-containing fluid at flow rates in the nanoliter per minute range provides for accurate quantitation after proper calibration, and the high sensitivity for an analyte contained within the fluid when combined with mass spectrometry. Systems and devices including a miniaturized and consolidated micro-column and micro-column array having affinity chromatographic adsorbents, which offer high selectivity and sensitivity, and accurate qualitative analysis as front ends to MS have been reported (U.S. Pat. Nos. 6,811,689; 6,020,208; 6,579,719).

Masses of relatively high molecular weight compounds such as antibodies can be detected at mass-to-charge ratios (m/z) that are easily determined by most mass spectrometers (typical m/z ranges of up to 2000 to 3000). Electrospray ionization mass spectrometry ESI-MS, in particular, is suited for charged, polar or basic compounds and for analyzing multiply charged compounds with excellent detection limits. ESI thus allows detection and characterization of large biomolecules, such as antibodies and antibody-drug conjugates with molecular weight (MW) of 150,000 or higher. With high-mass ions, a series of multiply charged molecular ions are typically observed. The molecular weight for positive ions is determined by multiplying the measured m/z ratio with the number of charges (n) minus the mass of the cation (C+) times the number of charges (n) on that ion.

The ESI method allows the presence or absence of fragmentation to be controlled by controlling the interface lens potentials. Electrospray ionization (ESI) is compatible with liquid separation methods (front end), as well as mass spectrometric detection methods (back end) ("Electrospray Ionization Mass Spectrometry: Fundamentals, Instrumentation, and Applications", Cole, R. B., Ed. (1997) Wiley, New York.

ESI-MS data may be acquired by averaging a number of scans together and smoothing the data to provide good peak intensity and shape. For low-mass compounds, the most abundant peaks observed are often the [M+H]+ ions in the positive-ion mode and [M−H]− in the negative ion mode. Doubly and triply charged ions as well as dimers may also be observed. Doubly charged positive ions will be observed at a mass (MW+2C+)÷2 where MW is the molecular weight and C+ is the ionizing cation, such as $H^+$, $Na^+$, or $NH4^+$. Except for the very low mass compounds, the detected ions will be multiply charged. Due to the soft (low ionizing potential) conditions of ESI, typically only molecular ions are observed. ESI spectra may have several molecular ion peaks that differ in the mass to charge ratio due to various numbers of charges the ion possesses.

A dilute solution of a sample, e.g. ADC or other biomolecule may be slowly pumped through a hypodermic needle for ESI-MS analysis. The sample may be introduced via flow injection or LC/MS. Typical flow rates range from less than 1 microliter (μl) per minute up to about one milliliter (ml) per minute. ESI is particularly suited for large biological molecules that are otherwise difficult to vaporize or ionize. The needle is held at a high voltage and the strong electric field at the end of the needle charges the nebulized solution and creates charged droplets. The charged droplets evaporate water to ultimately yield molecular ions that travel into the vacuum chamber through a small orifice. During the process of solvent evaporation, the non-covalently bound complex is transferred from solution to gas phase. (Hu et al (1994)). Gentle desolvation conditions are generally required to maintain the intact gas-phase complex. The orifice may be heated to ensure that the ions are completely desolvated. Some MS systems may employ a counter-flowed heated gas. Charged droplets are emitted from a hypodermic needle and shrink as they evaporate solvent before entering a vacuum chamber. Heat and gas flows may be used to aid desolvation. The amount of sample required for ESI measurements may be reduced by reducing the fluid flow by use of small capillary electrospray emitter, tips, a process known as nanoelectrospray. Nanoelectrospray methods can produce a constant signal for about 10-30 minutes for a 1 μl sample. The low flow has been shown to increase the ion efficiency and reduce ion suppression. Nanoelectrospray methods are frequently used for MS/MS protein studies (Korner et al (1996) J. Am. Soc. Mass Spectrom. 7:150-156; Mann, M. and Wilm, M. (1996) Anal. Chem. 68:1-8.

ESI of proteins produce multiply charged ions with the number of charges tending to increase as the molecular weight increases. The number of charges on a given ionic species may be determined by methods such as: (i) comparing two charge states that differ by one charge and solving simultaneous equations; (ii) looking for species that have the same charge but different adduct masses; and (iii) examining the mass-to-charge ratios for resolved isotopic clusters. The methods of ESI and ESI-MS and parameters needed to conduct these methods are well known in the art. The gentleness of the electrospray ionization process allows intact antibody conjugates to be directly detected by mass spectrometry.

In one embodiment, a Q1 mass spectrum of the protein, antibody, antibody fragment or antibody-conjugates (large molecules) is run as part of the method. A suitable quality Q1 mass spectrum of a large molecule can be obtained. Since there is potential for the protein envelope to shift, all the solvents used for chromatography are made fresh and acid is added to the elution solvent to position the spectrum envelop in the observed range. For proteins of ≥100,000 mass units, an acid such as formic acid can be used at about 0.1% (volume) in the elution solvents, for example, both solvent A (water) and B (acetonitrile). A stronger acid can be used, such as trifluoroacetic acid (TFA), at 0.05% (volume) TFA for both A and B solvents for proteins with ≤100,000 mass units. As the amount of formic acid is decreased, the intact glycosylated antibody, trastuzumab, picks up more charge, shifting the envelope further to the left and into the observed range of m/z (1800-3000 m/z). As the declustering potential (DP) voltage is increased from about 30-120V to about 70-190V, the charge on the antibody increases even further. Thus voltage applied, solvent composition, and ion pairing agents are factors to consider and adjust. The declustering potential (DP) may be increased (ramped) to acquire enough resolution to select the best charge ion range. Linearity may be obtained over a wide range of m/z. Deglycosylation of the antibody assists quantitation of intact antibody or heavy chain, fragments or ADC. Glycosylation contributes to lower ionization efficiency and thus reduced sensitivity. When quantitating antibody or antibody fragment conjugates, deglycosylation of the antibody may reduce the heterogeneity of the mass spectrum, increase sensitivity and thus simplifying the analysis.

Deconvolution tables are used to determine the exact mass to charge ratio (m/z) for each species to quantitated. Deconvolution software applications such as Analyst™ QS (Applied Biosystems, Foster City, Calif.) are commercially available and/or provided with mass spectrometers. Deconvolution software generally provides the user with a table of deconvoluted masses as well as a sub-table of m/z ions used to calculate these masses.

EXAMPLES

Example 1

Analysis of Anti-MUC 16 Antibody-drug Conjugate Compounds in Plasma and Serum

An anti-MUC16 antibody-drug conjugate, 3A5-MC-vc-PAB-MMAE, "Anti-MUC16 ADC" having the structure:

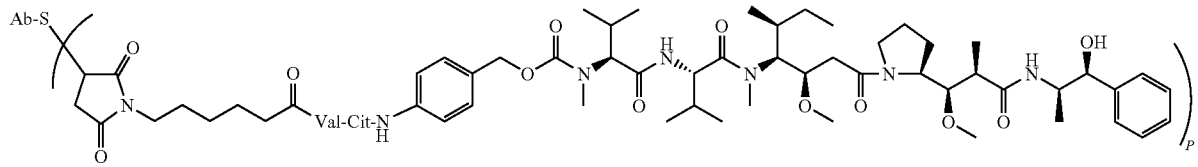

where p (DAR) is 1, 2, 3, or 4, Val is valine, Cit is citrulline, and Ab is a cysteine engineered, A118C heavy chain mutant variant of 3A5, an anti-MUC16 monoclonal antibody, was analyzed in plasma and serum samples. The 3A5 antibody variant recognizes epitopes on the extracellular domain (ECD) of MUC16, a cell surface transmembrane protein that is over-expressed in human epithelial ovarian cancers (EOCs) compared with normal human tissues, and is internalized upon binding to MUC16 and trafficked to lysosomes, thereby allowing targeted delivery of auristatin drug moiety MMAE to MUC16-positive tumor cells (WO 2007/001851; U.S. Ser. No. 60/916,657, filing date 8 May 2007, "CYSTEINE ENGINEERED ANTI-MUC16 ANTIBODIES AND ANTIBODY DRUG CONJUGATES"). The A 118C (EU numbering) mutant was selected for its optimized thiol reactivity with drug-linker reagents according to US 2007/0092940.

Anti-MUC16 ADC (3A5-MC-vc-PAB-MMAE) was characterized by the following immunoaffinity bead capture and mass spectrometry methods to measure the relative amounts of ADC sample constituents with different drug-to-antibody ratios (DAR) in plasma or serum. The method successfully identified the expected ADC sample constituents in the concentration range tested (1.25-50 μg/mL in a sample volume of 50 μL), indicating there were no selective losses during the affinity capture MS characterization. No significant matrix effects were observed across plasma or serum from different species. Results from rat, cynomolgus monkey and human plasma were comparable with those obtained from spiked anti-MUC16 ADC mixtures in PBS buffer with 5% BSA. Comparable results were also obtained from plasma and serum samples in both rat and cynomolgus monkey matrices. Short term matrix freeze/thaw stability was established for anti-MUC16 ADC (3A5-MC-vc-PAB-MMAE) mixtures in both rat plasma (up to 3 cycles) and cynomolgus serum (up to 6 cycles). Processed samples kept in an autosampler set to maintain 2° C.-8° C. for approximately 13 hours were stable.

The assay performance of the immunoaffinity bead/MS method was characterized for measuring the relative amounts of anti-MUC16 ADC mixtures with different drug loading values, p=0 (naked antibody), 1 (one drug per antibody), and 2 (two drugs per antibody) values, in plasma or serum. Standards of the naked antibody (p=0) and ADC (p=1 and 2) were combined to obtain mixtures of known composition. The standard mixtures were spiked into plasma (rat, cynomolgus monkey and human) and serum (e.g. rat and cynomolgus monkey) and recovered by affinity capture with biotinylated rhu MUC16 ECD immobilized onto streptavidin-coated paramagnetic beads. The captured anti-MUC16 ADC constituents were washed, deglycosylated, and eluted from the beads and analyzed by capillary flow LC coupled with quadrupole time-of-flight mass spectrometric detection. A representative time window of the total ion chromatogram (TIC) containing signals from the anti-MUC16 ADC constituents was selected to obtain the extracted mass spectrum. Following deconvolution of the mass spectrum, peak areas for the anti-MUC16 ADC constituents with p=0, 1, or 2 were used to calculate the relative amounts of anti-MUC16 ADC with different drug loading (p) in plasma or serum.

Biotinylated human MUC16 ECD was immobilized onto streptavidin coated beads, and used to capture Anti-MUC16 ADC by incubating with the study plasma or serum samples at room temperature. For example, the beads may be SEPHAROSE® beads of approximately 10-100 micron diameter. If the beads are paramagnetic, after binding of the sample constituents, the paramagnetic beads are held in place by the magnet, allowing for segregation, isolation, and washing of the sample constituents bound to the beads. If the beads are not paramagnetic, the beads may be configured in a column with an inlet and outlet for mobile phase flow. The sample constituents may be eluted as the processed analysis sample with an elution media or buffer, for example, with elevated acid and organic concentrations, and the eluted sample may be collected for application to the separation media to effect separation of the sample constituents followed by mass spectrometry. Typical non-specific wash buffer is aqueous and may include sodium acetate and sodium chloride at about pH 7.4. Typical antibody sample elution buffer is aqueous and may contain a low molecular alcohol such as isopropanol, acetonitrile, or other organic solvent, and an acid such as formic acid, at a pH of 2-4. After elution, the immobilized ECD beads may be collected, reused, or disposed of.

Alternatively, the SEPHAROSE® beads may bear an amino-reactive functionality such as NHS (N-hydroxysuccinimide) ester may be reacted (coupled) with ECD protein. The reactive amino groups of the ECD protein, such as lysine side chains, displace the NHS group, forming a stable amide bond between the ECD and bead. A typical coupling buffer is aqueous may include salts selected from phosphate, sodium bicarbonate and sodium chloride at or near neutral pH, e.g. pH 7-9. Surplus, uncoupled reactive functionality may be capped with a low molecular weight reactive amine, such as ethanolamine in aqueous media and may include salts selected from sodium bicarbonate and sodium chloride at or near neutral pH, e.g. pH 7-9.

The beads may be configured in a column format, with an inlet and exit for wash elution solutions. A commercially-available embodiment of NHS-activated SEPHAROSE® beads includes an NHS HiTrap HP 1.0 ml affinity column (Amersham).

Following affinity capture, bound anti-MUC16 ADC (3A5-MC-vc-PAB-MMAE) was isolated and deglycosylated. The latter step was used to reduce the sample heterogeneity and simplify the mass spectra. After several washes to remove non-specifically bound plasma proteins, the Anti-MUC16 ADC sample constituents were eluted by water containing 30% acetonitrile and 1% formic acid and injected onto a reversed-phase capillary LC system. Sample constituents (analytes) were ionized by turbo ionspray and detected by a quadrupole time-of-flight Q-Star XL mass spectrometer operated in the positive TOF-MS mode. A representative time window of the total ion chromatogram (TIC) was selected to obtain the mass spectrum. Mass spectrum was deconvoluted, and peak areas were obtained for each Anti-MUC16 ADC sample constituent of interest. The relative ratios of the anti-MUC16 ADC sample constituent p=0, 1, and 2 were calculated.

The following assay parameters were evaluated:

Ionization efficiency: anti-MUC16 ADC (3A5-MC-vc-PAB-MMAE) reference standards with specific p=0, 1, and 2 (DAR-0, DAR-1 and DAR-2, respectively) were mixed at different ratios (e.g. 33:33:33 and 30:60:10). The mixture was then incubated at 37° C. overnight for deglycosylation. The deglycosylated mixture was diluted to approximately 30 µg/mL and a 10 µL aliquot was injected directly onto LC/MS for analysis.

The total ion chromatogram of anti-MUC16 ADC (3A5-MC-vc-PAB-MMAE) sample constituents with p=0, 1, and 2 (DAR-0, DAR-1 and DAR-2) at a ratio of 30:60:10 in HBS-EP was obtained and a representative time window containing the ADC signals was selected. The time windows may shift due to variations in the LC conditions. The corresponding mass spectrum was extracted displaying the characteristic charge envelope for the ADC sample constituents. Deconvolution of the mass spectrum generated a peak area table with the corresponding deconvoluted mass spectrum. Based on the molecular masses of anti-MUC16 ADC sample constituents, three main peaks were identified as DAR-0, DAR-1 and DAR-2 at approximately 144,834 Da, 146,033 Da and 147,223 Da, respectively. Without internal calibration, the mass accuracy of the instrument was about ±50 Da. Other minor peaks were largely due to matrix background, adducts, and/or heterogeneity of the reference materials. They did not result in any significant impact to the calculation of relative amounts of ADC sample constituents, and were thus not used in subsequent ratio calculations. The three individual peak areas were summed as the total peak area, and the relative percent ratio of each anti-MUC16 ADC sample constituent was calculated. The data are summarized in Table 1A and 1B (below) for the two spike mixtures, respectively. Three replicates were tested for each spike composition. Clearly, mean accuracy was within the range of 70% to 130%. It was therefore concluded that anti-MUC16 ADC sample constituents with DAR-0, DAR-1 and DAR-2 did not demonstrate any significant difference in their ionization efficiency in the positive turbo ionspray mode.

TABLE 1

Relative Ratios of anti-MUC16 ADC (3A5-MC-vc-PAB-MMAE) sample constituents in HBS-EP Buffer Measured Directly by LC/MS for Known Mixtures of DAR 0, DAR 1, and DAR 2

| | A: | | | | B: | | |
|---|---|---|---|---|---|---|---|
| Spiked (%) | Measured (%) | | | Spiked (%) | Measured (%) | | |
| DAR0/DAR1/DAR2 | DAR 0 | DAR 1 | DAR 2 | DAR0/DAR1/DAR2 | DAR 0 | DAR 1 | DAR 2 |
| 33/33/33 | 30 | 38 | 32 | 30/60/10 | 31 | 61 | 8 |
| | 31 | 36 | 33 | | 31 | 60 | 9 |
| | 31 | 37 | 32 | | 31 | 61 | 8 |
| Mean | 31 | 37 | 32 | Mean | 31 | 61 | 8 |
| SD | 0.4 | 0.8 | 0.6 | SD | 0.1 | 0.5 | 0.6 |
| RSD (%) | 1.1 | 2.3 | 1.7 | RSD (%) | 0.4 | 0.8 | 7.4 |
| Accuracy (%) | 93 | 110 | 97 | Accuracy (%) | 103 | 101 | 82 |

Selectivity: To confirm there were no selective losses during the affinity capture of DMUC4064A components with rhuMUC16 ECD, known DMUC4064A standards with different DAR were spiked at various concentrations into rat plasma and analyzed by affinity MS. Table 2 shows the measured ratios vs. theoretical spike ratios for DAR-0, DAR-1 and DAR-2 at 10:30:60, 30:60:10 and 33:33:33, respectively.

TABLE 2

Measured Ratios vs. Spike Ratios for anti-MUC16 ADC (3A5-MC-vc-PAB-MMAE) sample constituents in Rat Plasma Measured by Affinity MS

| Spike Ratio (%) | Measured Ratio (%) | | |
|---|---|---|---|
| DAR 0/DAR 1/DAR 2 | DAR 0 | DAR 1 | DAR 2 |
| 10/30/60 | 11 | 31 | 59 |
| | 10 | 30 | 60 |
| | 11 | 30 | 59 |
| Mean | 11 | 30 | 59 |
| SD | 0.9 | 0.6 | 0.6 |
| RSD (%) | 8.6 | 1.9 | 0.9 |
| Mean Accuracy (%) | 106 | 101 | 99 |
| 30/60/10 | 28 | 62 | 9 |
| | 30 | 61 | 9 |
| | 30 | 60 | 10 |
| Mean | 29 | 61 | 10 |
| SD | 0.8 | 1.0 | 0.2 |
| RSD (%) | 2.8 | 1.6 | 2.1 |
| Mean Accuracy (%) | 98 | 102 | 95 |
| 33/33/33 | 28 | 34 | 38 |
| | 28 | 34 | 38 |
| | 28 | 34 | 38 |
| Mean | 28 | 34 | 38 |
| SD | 0.1 | 0.4 | 0.3 |
| RSD (%) | 0.5 | 1.3 | 0.9 |
| Mean Accuracy (%) | 84 | 102 | 117 |

The mean accuracy was within the range of 70% to 130% for three anti-MUC16 ADC sample constituents of DAR-0, DAR-1 and DAR-2 at different compositions, indicating that ECD modified affinity beads were able to recover ADCs without selective losses from plasma, and demonstrated acceptable accuracy.

Matrix effects across different species: Anti-MUC16 ADC (3A5-MC-vc-PAB-MMAE) reference standards with specific p=0, 1, and 2 were spiked at a ratio of 30:60:10 into rat, cynomolgus monkey and human plasma or into PBS buffer with 5% BSA. A total ADC concentration of 30 μg/mL was used. Three replicates for each plasma species were recovered by ECD modified affinity beads and compared with the results from PBS buffer with 5% BSA, which was used as control. The blank rat, cynomolgus monkey and human plasma treated by ECD affinity capture and the anti-MUC16 ADC sample constituents were analyzed by TIC (total ion chromatography. No significant analyte peaks were found in the typical ADC time window. The extracted TOF MS signals were also too low to be deconvoluted, indicating the affinity capture by human MUC16 ECD was relatively clean and subjected to minimal impacts by non-specific proteins from the plasma matrices.

Representative TIC chromatograms for anti-MUC16 ADC sample constituents spiked into rat, cynomolgus monkey and human plasma were compared with that of PBS buffer control. Chromatographic patterns for anti-MUC16 ADC sample constituents in these four matrices captured by ECD immunoaffinity bead were very similar. Similar DAR distribution patterns obtained from the representative chromatographic retention time window were observed among the three species plasma matrices and the PBS (Buffer) control. The sample constituents were assigned DAR 0 (+0, naked antibody), DAR-1 (+1D, one MC-vc-PAB-MMAE drug linker unit) and DAR-2 (+2D, two MC-vc-PAB-MMAE drug linker units). Detailed comparison of the relative amounts of DAR-0, DAR-1 and DAR-2 components are shown in Table 3. The overall Relative Standard Deviation (RSD) was well below 30% for all four matrices tested. Therefore the affinity MS method showed minimal matrix effects across different species. The overall accuracy was within the range of 70 to 130%.

TABLE 3

Precision and accuracy for Anti-MUC16 ADC (3A5-MC-vc-PAB-MMAE) spiked in various plasma across different species and PBS Buffer

| DAR 0/DAR 1/DAR 2 (30/60/10) | % DAR 0 | % DAR 1 | % DAR 2 |
|---|---|---|---|
| Rat Plasma | 31 | 57 | 12 |
| | 28 | 60 | 12 |
| | 29 | 59 | 12 |
| Mean (Rat Plasma) | 30 | 59 | 12 |
| SD (Rat Plasma) | 1.5 | 1.6 | 0.1 |
| Cynomolgus Monkey Plasma | 27 | 59 | 13 |
| | 29 | 58 | 13 |
| | 29 | 58 | 13 |
| Mean (Cyno Plasma) | 29 | 58 | 13 |
| SD (Cyno Plasma) | 1.1 | 0.8 | 0.3 |
| Human Plasma | 29 | 59 | 12 |
| | 29 | 60 | 11 |
| | 29 | 59 | 12 |
| Mean (Human Plasma) | 29 | 59 | 12 |
| SD (Human Plasma) | 0.1 | 0.7 | 0.6 |
| PBS w. 5% BSA | 29 | 59 | 12 |
| | 28 | 59 | 12 |
| | 27 | 60 | 13 |

TABLE 3-continued

Precision and accuracy for Anti-MUC16 ADC
(3A5-MC-vc-PAB-MMAE) spiked in various plasma
across different species and PBS Buffer

| DAR 0/DAR 1/DAR 2 (30/60/10) | % DAR 0 | % DAR 1 | % DAR 2 |
|---|---|---|---|
| Mean (PBS) | 28 | 60 | 12 |
| SD (PBS) | 1.2 | 0.7 | 0.6 |
| Overall Mean (4 Matrices, n = 12) | 29 | 59 | 12 |
| Overall SD (n = 12) | 1.1 | 1.0 | 0.7 |
| Overall RSD (%), n = 12 | 3.8 | 1.7 | 5.5 |
| Overall Accuracy (%), n = 12 | 96 | 98 | 122 |

Matrix effects between plasma and serum: anti-MUC16 ADC (3A5-MC-vc-PAB-MMAE) reference standards with specific p=0, 1, and 2 were spiked at a ratio of 30:60:10 into both plasma and serum matrices of rat and cynomolgus monkey. Comparable deconvoluted mass spectra were observed across serum and plasma matrices in each case. The values obtained for DMUC4064A mixtures of known composition with DAR 0, DAR 1, and DAR 2 in plasma and serum matrices are shown in Table 4. The overall RSD in rat matrices was well within the acceptable range of 30%, indicating no bias occurred during affinity capture by ECD between rat plasma and serum. Similarly, overall RSD in cynomolgus monkey matrices was <30%, showing no bias between cynomolgus monkey plasma and serum.

TABLE 4

Precision determination of anti-MUC16 ADC
(3A5-MC-vc-PAB-MMAE) sample constituents in
plasma and serum from rat and cynomolgus monkey

| Spike Ratio (%) | Measured Ratio (%) | | |
|---|---|---|---|
| DAR 0/DAR 1/DAR 2 (30/60/10) | DAR 0 | DAR 1 | DAR 2 |
| Rat Plasma | 31 | 57 | 12 |
|  | 28 | 60 | 12 |
|  | 29 | 59 | 12 |
| Mean | 30 | 59 | 12 |
| SD | 1.5 | 1.6 | 0.1 |
| Rat Serum | 28 | 58 | 13 |
|  | 25 | 61 | 14 |
|  | 28 | 59 | 14 |
| Mean | 27 | 59 | 14 |
| SD | 2.1 | 1.8 | 0.3 |
| Overall Mean in Rat (n = 6) | 28 | 59 | 13 |
| Overall SD in Rat (n = 6) | 2.2 | 1.6 | 1.1 |
| Overall RSD (%) in Rat (n = 6) | 7.8 | 2.7 | 8.7 |
| Cynomolgus Monkey Plasma | 27 | 59 | 13 |
|  | 29 | 58 | 13 |
|  | 29 | 58 | 13 |
| Mean | 29 | 58 | 13 |
| SD | 1.1 | 0.8 | 0.3 |
| Cynomolgus Monkey Serum | 27 | 60 | 13 |
|  | 30 | 57 | 13 |
|  | 28 | 60 | 13 |
| Mean | 28 | 59 | 13 |
| SD | 1.5 | 1.5 | 0.0 |
| Overall Mean in Cyno Monkey (n = 6) | 28 | 59 | 13 |
| Overall SD in Cyno Monkey (n = 6) | 1.2 | 1.2 | 0.3 |
| Overall RSD (%) in Cyno Monkey (n = 6) | 4.3 | 2.0 | 2.3 |

To further evaluate potential matrix effects between plasma and serum, a subset of in vivo cynomolgus monkey samples dosed with anti-MUC16 ADC (3A5-MC-vc-PAB-MMAE) were collected and analyzed using the immunoaffinity bead capture and mass spectrometry method. Plasma and corresponding serum samples collected between 5 minutes and 22 days post dose from a single animal were analyzed, and the results were compared (Table 5). The results indicate that there were no significant differences in relative DAR distributions of recovered anti-MUC16 ADC sample constituents between the cynomolgus monkey plasma or corresponding serum samples. FIG. 9 shows the example of deconvoluted mass spectrometry data of in vivo stability in cynomolgus monkey plasma dosed with 38 mg/kg Thio Hu Anti MUC16 (3A5) HC A118C-MC-vc-PAB-MMAE. The average drug loading was 1.6 MMAE/3A5. About 30% of the dosed ADC was a different form of DAR +1 than the one generated from the deconjugation of DAR2. Plasma samples were collected at 5 min, 6 hr, 24 hr, 72 hr, 6 day, 8 day, 15 day, and 22 day time points, and captured by immunoaffinity ECD bead method. The sample constituents were assigned DAR of +0 (naked antibody), +1D (one MC-vc-PAB-MMAE drug linker unit) and +2D (two MC-vc-PAB-MMAE drug linker units). The small peaks at about 149,000 and 150,000 amu are sample constituents undergoing incomplete deglycosylation.

TABLE 5

Relative DAR distributions of anti-MUC16 ADC (3A5-MC-vc-
PAB-MMAE) sample constituents in cynomolgus monkey serum
and plasma collected from a toxicology study

| Cyno TK 06-1226 Group 5, Animal 100415 | Cyno Serum Calculated ADC composition (%) | | | Cyno Plasma Calculated ADC composition (%) | | |
|---|---|---|---|---|---|---|
| Time | DAR 0 | DAR 1 | DAR 2 | DAR 0 | DAR 1 | DAR 2 |
| 5 min. | 0 | 10 | 90 | 0 | 9 | 91 |
| 6 hr | 0 | 21 | 79 | 0 | 20 | 80 |
| 24 hr | 7 | 31 | 62 | 7 | 31 | 62 |
| 72 hr | 14 | 41 | 46 | 15 | 39 | 46 |
| 6 day | 20 | 44 | 36 | 19 | 44 | 37 |
| 8 day | 21 | 45 | 34 | 21 | 45 | 34 |
| 15 day | 31 | 49 | 20 | 30 | 49 | 21 |
| 22 day | 41 | 44 | 15 | 42 | 45 | 14 |

FIG. 6 shows deconvoluted mass spectrometry data of stability of Thio Hu Anti MUC16 (3A5) HC A118C-MC-vc-PAB-MMAE (100 μg/ml in rat plasma incubated at 37° C.) samples collected at 0, 6, 24, 48, and 96 hour time points after ECD immunoaffinity bead capture. The sample constituents were assigned drug/antibody ratio (DAR) of +0 (naked antibody), +1D (one MC-vc-PAB-MMAE drug linker unit) and +2D (two MC-vc-PAB-MMAE drug linker units). FIG. 7 shows the DAR distribution change over time of sample constituents DAR +0, +1, and +2 in rat plasma.

ECD immunoaffinity bead capture efficiency was compared with anti-drug Mab immunoaffinity bead capture of Thio Hu Anti MUC16 (3A5) HC A118C-MC-vc-PAB-MMAE after incubation in rat plasma. Four different anti-auristatin monoclonal antibody clones were biotinylated and immobilized on streptavidin coated paramagnetic beads (FIG. 2). These anti-drug clones showed inefficient capture of one-drug loaded ADC (DAR +1).

Example 2

ECD Immunoaffinity Bead Capture Protocol

The serum and plasma samples from cynomolgus monkey dosed with the anti-MUC16 antibody-drug conjugate, 3A5-MC-vc-PAB-MMAE, were processed by the following steps:
1 Determine the plate location for samples, controls and blanks (96 deep well plate (2 mL square top): Analytical Sales and Service Inc. Cat. No. 59623-23, or 96 well plate (500 μL round top): VWR Cat No. 47743-828). Typically, two blanks and one system control are tested at the beginning of the run, followed by samples, and two blanks and two system controls are tested at the end of the run. Additional blanks can be tested throughout the run if desired. The additions to the wells described below are done for the wells that are used for a sample, control or blank.
2. Pipette 400 μL HBS-EP buffer (Biacore Cat. No. BR-1001-88) into each well of a 96 deep well square top plate that will be used for sample, control or blank.
3. Resuspend streptavidin coated Dynabeads M-280 (Dynabeads, M280 streptavidin, 10 mg/mL, Cat. No. 110029, Lot No. G74050, BioVeris) by gently shaking. Pipette 100 μL suspended bead mixture into the HBS-EP buffer plate into each well in use. Mix by KingFisher 96 Magnetic particle processor (Thermo Electron Corp.) at room temperature for approximately 20 seconds.
4. Transfer the beads to a new 96 deep well square top plate containing 400 μL HBS-EP buffer and mix by KingFisher at room temperature for approximately 20 seconds.
5. Pipette 400 μL HBS-EP buffer into each blank, sample, or control well of a new 96 deep well square top plate.
6. Pipette 25 μL of biotinylated anti-MUC16-ECD (FIG. 1a) into each blank, sample, or control well of the HBS-EP buffer plate.
7. Transfer the beads into the 96 deep well plate containing HBS-EP buffer and biotinylated anti-MUC16-ECD and gently mix for approximately 20 seconds. Cover the plate with an aluminum seal.
8. Place the plate on a shaker (set to speed 7) and incubate at room temperature for approximately 120 minutes.
9. Transfer the beads into a 96 deep well square top plate containing 400 μL HBS-EP buffer and wash two times using the KingFisher.
10. Dilute the plasma or serum samples into the range of the assay using negative plasma or serum pool.
11. Pipette 400 μL HBS-EP buffer into a 96 deep well square top plate, and then add 50 μL of each diluted plasma or serum sample, control or blank to the appropriate wells.
12. Transfer the beads into the diluted plasma or serum sample using the KingFisher. Gently mix for approximately 20 seconds. Cover the plate with an aluminum seal tape.
13. Place the plate on a shaker (at speed 7) and incubate at room temperature for approximately 120 minutes.
14. Transfer the beads into a 96 deep well square top plate containing 500 μL HBS-EP buffer and wash two times using the KingFisher.
15. Prepare HBS-EP-glycanase buffer by mixing HBS-EP buffer, 80 mM phosphate, and Glyko N-glycanase (Prozyme glyko N-glycanase, Cat. No. GKE-5006D) at a ratio of 300 parts:32 parts:4 parts respectively.
16. Pipette 336 μL HBS-EP-glycanase buffer into each well of a 96 deep well square top plate.
17. Transfer the beads into the HBS-EP-glycanase buffer using the KingFisher. Gently mix for approximately 20 seconds. Cover the plate with an aluminum seal tape.
18. Place the plate in an incubator set to maintain 37° C. and shaking speed set to 300 rpm and incubate overnight.
19. Transfer the beads into a 96 deep well square top plate containing 500 μL HBS-EP buffer and wash two times using the KingFisher.
20. Transfer the beads into a 96 deep well square top plate containing 500 μL water and wash two times using the KingFisher.
21. Transfer the beads into a 96 deep well square top plate containing 500 μL 10% acetonitrile in water and wash one time using the KingFisher.
22. Pipette 50 μL of 30% acetonitrile in water with 1% formic acid into a 96 deep well square top plate as the elution solvent.
23. Transfer the beads into the elution solvent plate using the KingFisher. Cover the plate with an aluminum seal tape.
24. Place the plate on a shaker set to speed 7 and shake for approximately 15 minutes.
25. Remove the beads from the elution plate using the KingFisher.
26. Transfer the supernatant from the elution plate into a 96-well injection plate (VWR, 500 μL round top) using a multichannel pipet and cover the plate with a silicon sealing mat.
27. Centrifuge at a setting of 3000 rpm for approximately 5 minutes with the centrifuge set to maintain 2-8° C. The sample plate is then ready for injection onto LC-MS.

Example 3

Analysis of Anti-HER2 Antibody-drug Conjugate (ADC) Compounds in Plasma and Serum Cysteine engineered anti-HER2 variants V205C and A118C trastuzumab-MC-vc-PAB-MMAE having the structure:

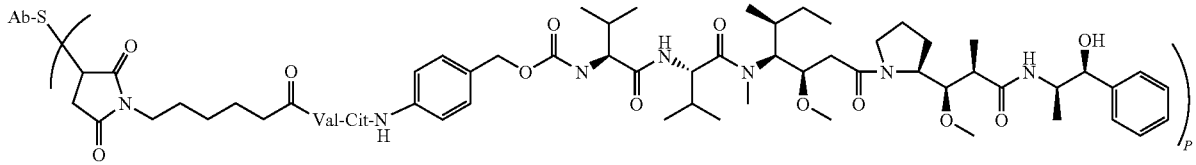

where p is 1, 2, 3, or 4, Val is valine, Cit is citrulline, and Ab is a cysteine engineered, A118C heavy chain mutant variant and V205C light chain mutant of trastuzumab, an anti-HER2 monoclonal antibody, were analyzed in plasma samples.

FIG. 4 shows changes in the drug/antibody ratio (DAR) distribution for: (top) light chain (Thio Hu Anti HER2 4D5 LC V205C-MC-vc-PAB-MMAE, 1.64 MMAE/4D5 Ab), and (bottom) heavy chain (Thio Hu Anti HER2 4D5 HC A118C-MC-vc-PAB-MMAE, 1.9 MMAE/4D5 Ab) ADC variants in plasma after immunoaffinity ECD bead capture (FIG. 1a) and mass spectrometry characterization from in vivo plasma samples collected at 0, 8, 24, 48, and 96 hour time points. The sample constituents were assigned DAR of 0 (naked antibody), 1 (one MC-vc-PAB-MMAE drug linker unit) and 2 (two MC-vc-PAB-MMAE drug linker units). The DAR distribution pattern indicates that, for these ADC, the light chain variant (LC V205C) is more stable than the heavy chain variant (HC A118C).

Figure 5:
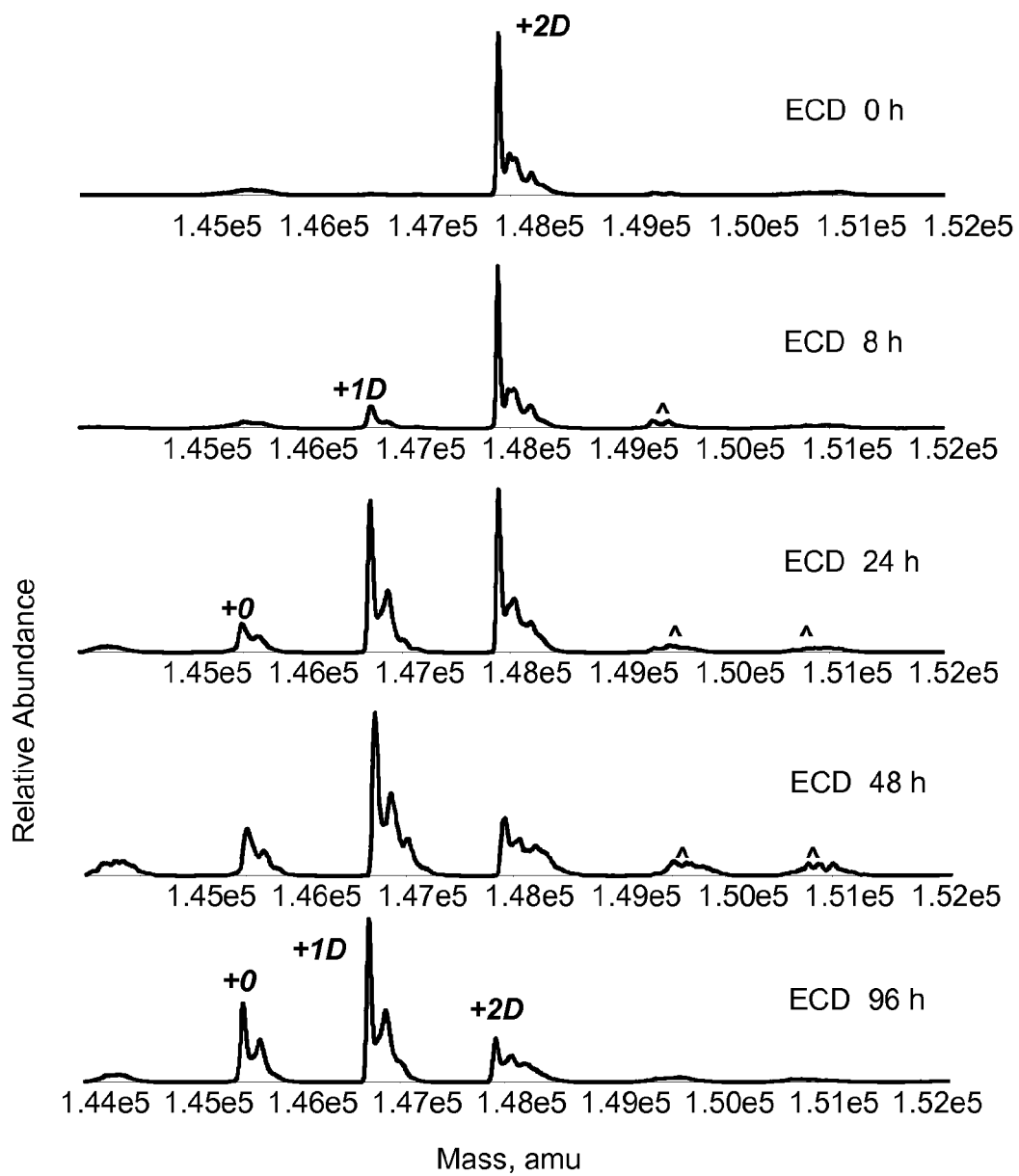
FIG. 5 shows deconvoluted mass spectrometry data of stability of Thio Hu Anti HER2 4D5 HC A118C-MC-vc-PAB-MMAE (100 µg/ml in rat plasma incubated at 37° C.) samples collected at 0, 8, 24, 48, and 96 hour time points, as plotted in FIG. 4 (bottom). The sample constituents were assigned DAR of +0 (naked antibody), +1D (one MC-vc-PAB-MMAE drug linker unit) and +2D (two MC-vc-PAB-MMAE drug linker units). The small peaks at about 151,000 amu are sample constituents undergoing incomplete deglycosylation.

The heavy chain variant (Thio Hu Anti HER2 4D5 HC A118C-MC-vc-PAB-MMAE, 1.9 MMAE/4D5 Ab) was incubated in rat plasma at 100 µg/ml. Samples were collected at certain time points and processed by immunoaffinity ECD bead capture. FIG. 5 shows deconvoluted mass spectrometry data of samples collected at 0, 8, 24, 48, and 96 hour time points. The sample constituents were assigned DAR of +0 (naked antibody), +1D (one MC-vc-PAB-MMAE drug linker unit) and +2D (two MC-vc-PAB-MMAE drug linker units). The small peaks at about 151,000 amu are sample constituents undergoing incomplete deglycosylation.

Example 4

Comparison of ELISA and Immunoaffinity Bead Capture Methods

Figure 10A:
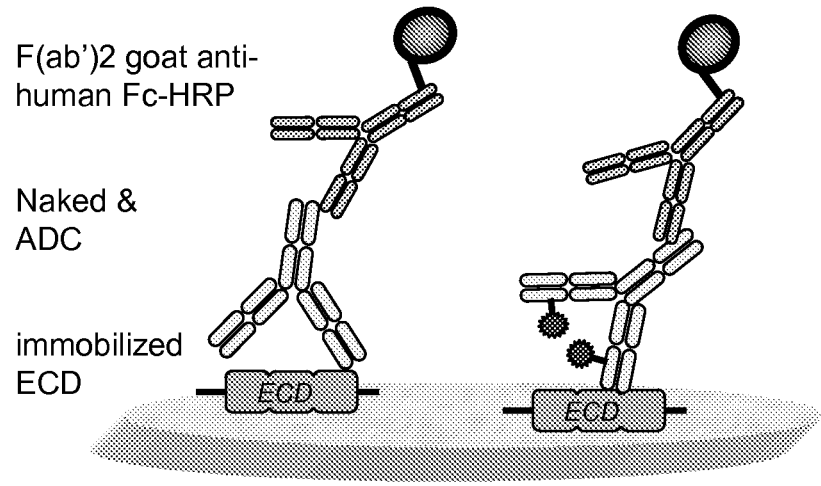
FIG. 10a shows a Total ELISA assay format whereby ECD of a receptor is immobilized on a solid support for binding to antibody or antibody-drug conjugate (ADC). The ADC binds to a F(ab')2 goat anti-human Fc-HRP (horse radish peroxidase) for chemiluminescent detection.

FIG. 10a shows a Total ELISA assay format whereby ECD protein is immobilized on a solid support for binding to antibody or antibody-drug conjugate (ADC). The ADC binds to a F(ab')2 goat anti-human Fc-HRP for chemiluminescent detection.

Figure 10B:
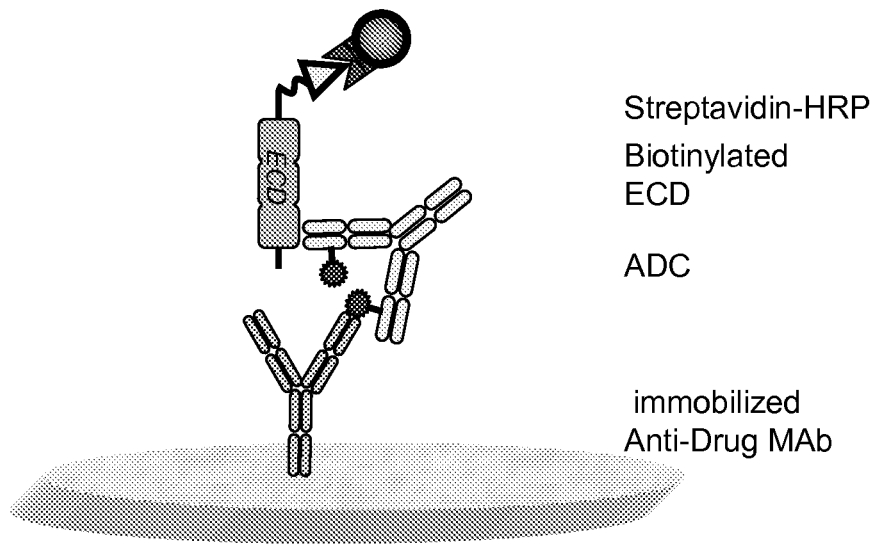
FIG. 10b shows a conjugate ELISA assay format whereby an anti-drug MAb is immobilized on a solid support for binding to an antibody-drug conjugate (ADC). The ADC binds to a biotinylated ECD of a receptor in solution. The complex can then bind to streptavidin-horse radish peroxidase (HRP) for chemiluminescent detection.

FIG. 10b shows a conjugate ELISA assay format whereby an anti-drug MAb is immobilized on a solid support for binding to an antibody-drug conjugate (ADC). The ADC binds to a biotinylated ECD protein in solution. The complex can then bind to streptavidin-horse radish peroxidase (HRP) for chemiluminescent detection.

FIG. 11 shows a comparison of detection of sample constituents by the ELISA method and by the immunoaffinity bead capture/mass spectrometry (MS) method by a plot of the antibody remaining conjugated to the drug moiety in rat plasma samples incubated with Thio Hu Anti MUC16 (3A5) HC A118C-MC-vc-PAB-MMAE and analyzed at time points up to 96 hours.

Table 6 compiles the relative amounts of Thio Hu Anti MUC16 (3A5) HC A118C-MC-vc-PAB-MMAE sample constituents from the same 0, 6, 24, 48, 96 time point samples captured by ECD immunoaffinity beads and analyzed by mass spectrometry. The results from affinity mass spectrometry and ELISA indicated that an anti-auristatin antibody did not efficiently capture all conjugated Thio Hu Anti MUC16 (3A5) HC A118C-MC-vc-PAB-MMAE sample constituents. Affinity MS can therefore be used to help screen the most appropriate anti-drug antibody for developing the conjugate ELISA assay.

TABLE 6

ECD Immunoaffinity Bead Capture
Sample constituents capture by ECD Immunoaffinity
Bead and Mass spectrometry detection

| Time hr | % DAR + 2 | % DAR + 1 | % DAR + 0 (naked Ab) | % Conjugate |
|---|---|---|---|---|
| 0 | 100 | 0 | 0 | 100 |
| 6 | 84 | 16 | 0 | 100 |
| 24 | 48 | 43 | 9 | 91 |
| 48 | 36 | 49 | 15 | 85 |
| 96 | 32 | 50 | 18 | 82 |

We claim:

1. A method for detecting antibody-drug conjugate compounds comprising:
   (i) providing an antibody-drug conjugate compound having Formula I:

Ab-(L-D)$_p$    I wherein Ab is an antibody, wherein the antibody is specific against an extracellular domain (ECD) of a target receptor protein;
   D is a maytansinoid or monomethylauristatin drug moiety;
   L is a linker covalently attached to Ab, and covalently attached to D; and
   p is 1, 2, 3, 4, 5, 6, 7, or 8;
   (ii) contacting the antibody-drug conjugate compound with a biological source selected from a mammal, tissue, cell culture, plasma or serum;
   (iii) collecting a biological sample that has been contacted by the antibody-drug conjugate from the biological source;
   (iv) processing the biological sample to form an analysis sample by formulating, immobilizing, centrifuging, isolating, digesting, inducing or preventing blood cell clotting, hydrolyzing, or purifying to form a processed analysis sample;
   (v) capturing the processed analysis sample on immunoaffinity beads comprising an antigen specific for the antibody of the antibody-drug conjugate, wherein the antigen is the extracellular domain (ECD) of the target receptor protein;
   (vi) eluting the processed analysis sample;
   (vii) applying the processed eluted analysis sample to a separation media to effect separation of more than one sample constituent by capillary liquid chromatography wherein a separated sample constituent comprises the antibody-drug conjugate compound;
   (viii) establishing the mass to charge ratio of one or more separated sample constituents by mass spectrometry wherein the intact antibody-drug conjugate is detected.

2. The method of claim 1 further comprising repeating steps (iii) to (viii) one or more times.

3. The method of claim 1 wherein the biological sample is blood and the blood is processed to form plasma or serum.

4. The method of claim 1 wherein the analysis sample is denatured.

5. The method of claim 1 wherein the analysis sample is denatured by a denaturing reagent selected from formamide, dimethylformamide and acetonitrile.

6. The method of claim 1 wherein the analysis sample is treated with a reducing agent.

7. The method of claim 6 wherein the reducing agent is DTT or TCEP.

8. The method of claim 1 wherein the ECD is biotinylated.

9. The method of claim 8 wherein the biotinylated ECD binds to streptavidin coated paramagnetic immunoaffinity bead.

10. The method of claim 1 wherein the antigen is an anti-drug antibody.

11. The method of claim 1 wherein the immunoaffinity bead is a magnetic bead.

12. The method of claim 1 wherein the immunoaffinity bead comprises a porous polymer monolith.

13. The method of claim 1 wherein the immunoaffinity bead is configured in a flow-through channel in fluid communication with a collection reservoir.

14. The method of claim 13 wherein the immunoaffinity bead is configured in a flow-through vessel wherein the sample from the biological source is introduced at one end or orifice, and a sample is eluted from another end or orifice.

15. The method of claim 14 wherein the immunoaffinity bead is distributed in a plurality of flow-through vessels, each in communication with a separate collection reservoir.

16. The method of claim 15 wherein the vessels and reservoirs are configured in a 96 microtitre well format of 12×8 columns and rows, or a 384 microtitre well format of 24×16 columns and rows.

17. The method of claim 1 further comprising the step of treating the analysis sample with a degycosylating reagent.

18. The method of claim 1 wherein the deglycosylating reagent is PNGaseF.

19. The method of claim 1 wherein the separation media is a chromatography support.

20. The method of claim 19 wherein the chromatography support is a reverse-phase adsorbent.

21. The method of claim 20 wherein the reverse phase is polystyrene, or a graft or copolymer of polystyrene.

22. The method of claim 20 wherein an effluent from the chromatography support is intermittently analyzed by mass spectrometry to establish the mass to charge ratio of more than one of the separated cleared constituents.

23. The method of claim 1 wherein the antibody-drug conjugate compound is administered to a mammal at a dose of 0.1 to 10 mg/kg body weight.

24. The method of claim 1 wherein L is covalently attached to an amino, carboxyl or thiol of Ab.

25. The method of claim 1 wherein L is formed from a linker reagent selected from N-succinimidyl-4(2-pyridylthio)propanoate (SPDP), succinimidyl-4-(N-maleimidomethyl) cyclohexane-1-carboxylate (SMCC) and N-succinimidyl-4-(2-pyridylthio)pentanoate (SPP).

26. The method of claim 1 wherein L is selected from maleimidocaproyl (MC), maleimidopropanoyl (MP), and maleimidocaproyl-valine-citrulline -para-aminobenzyloxycarbonyl(MC-vc-PAB).

27. The method of claim 1 wherein D is DM1, having the structure:

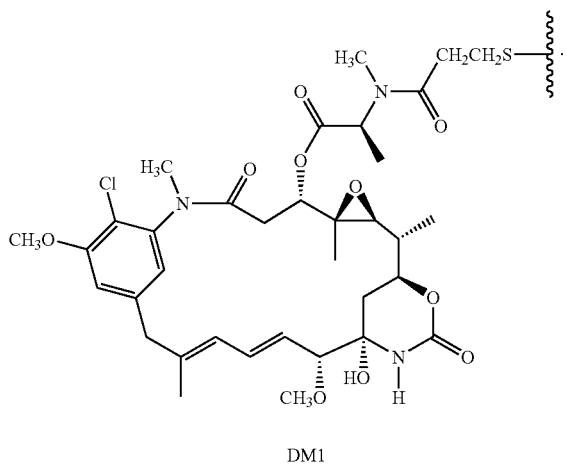

DM1

28. The method of claim 1 wherein D is a monomethylauristatin.

29. The method of claim 28 wherein D is MMAE, having the structure:

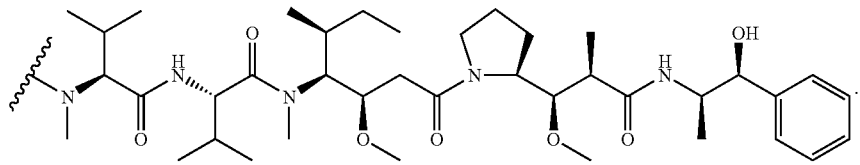 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

30. The method of claim 28 wherein D is MMAF, having the structure:

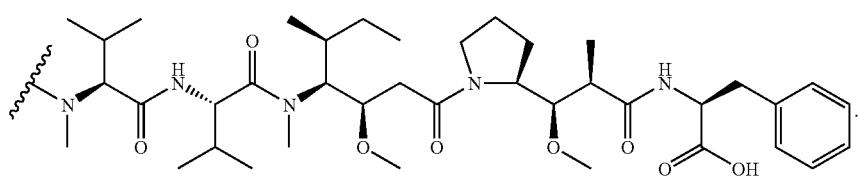 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

* * * * *